United States Patent [19]
Hartman et al.

[11] Patent Number: 5,786,373
[45] Date of Patent: Jul. 28, 1998

[54] FIBRINOGEN RECEPTOR ANTAGONISTS

[75] Inventors: George D. Hartman, Lansdale; John D. Prugh, Chalfont; Melissa S. Egbertson, Ambler; Mark E. Duggan, Schwenksville; William Hoffman, Lansdale, all of Pa.

[73] Assignee: Merck & Co., Inc., Rahway, N.J.

[21] Appl. No.: 416,772

[22] PCT Filed: Oct. 12, 1993

[86] PCT No.: PCT/US93/09750

§ 371 Date: May 31, 1995

§ 102(e) Date: May 31, 1995

[87] PCT Pub. No.: WO94/08577

PCT Pub. Date: Apr. 28, 1994

Related U.S. Application Data

[63] Continuation of Ser. No. 960,977, Oct. 12, 1992, abandoned.

[51] Int. Cl.$^6$ .......... A61K 31/38; A61K 31/415; A61K 31/44; A61K 31/445; C07D 333/22; C07D 233/64; C07D 401/12; C07D 409/06

[52] U.S. Cl. .......... 514/326; 514/327; 514/331; 514/336; 514/340; 514/341; 514/342; 514/398; 514/400; 514/438; 546/209; 546/210; 546/212; 546/280.4; 546/280.1; 546/280.7; 546/282.1; 546/282.4; 546/283.4; 546/283.7; 546/213; 546/281.4; 548/322.5; 548/323.1; 548/324.1; 548/324.5; 548/325.1; 548/375.1; 549/64; 549/65; 549/70; 549/72; 549/75; 549/76; 549/77

[58] Field of Search .......... 546/209, 210, 546/212, 280.4, 282, 213, 282.4, 280.1, 280.7, 283.4, 283.7, 281.4; 548/247, 248, 322.5, 323.1, 324.1, 324.5, 325.1, 375.1; 549/64, 65, 70, 72, 75, 76, 77; 574/326, 327, 331, 336, 340, 341, 342, 343, 365, 380, 398, 400, 438

[56] References Cited

U.S. PATENT DOCUMENTS

| | | | |
|---|---|---|---|
| 4,064,255 | 12/1977 | Champseix et al. | 424/267 |
| 5,039,805 | 8/1991 | Alig et al. | 546/224 |
| 5,064,814 | 11/1991 | Klein et al. | 574/18 |
| 5,084,466 | 1/1992 | Alig et al. | 514/353 |
| 5,227,490 | 7/1993 | Hartman et al. | 514/317 |
| 5,256,812 | 10/1993 | Alig et al. | 560/35 |
| 5,292,756 | 3/1994 | Duggan | 514/331 |
| 5,294,616 | 3/1994 | Duggan | 514/255 |
| 5,321,034 | 6/1994 | Duggan | 514/323 |
| 5,563,158 | 10/1996 | DeGrado | 514/340 |

FOREIGN PATENT DOCUMENTS

| | | |
|---|---|---|
| 0 352 249 | 1/1990 | European Pat. Off. |
| 0 372 486 | 6/1990 | European Pat. Off. |
| 0 381 033 | 8/1990 | European Pat. Off. |
| 0 384 362 | 8/1990 | European Pat. Off. |
| 0 405 537 | 1/1991 | European Pat. Off. |
| 0 478 328 | 4/1992 | European Pat. Off. |
| 0 478 362 | 4/1992 | European Pat. Off. |
| 0 478 363 | 4/1992 | European Pat. Off. |
| 0 479 481 | 4/1992 | European Pat. Off. |

OTHER PUBLICATIONS

Mardder VJ, Sherry S. New England Journal of Medicine, 318 (23), 1512, Jun. 1988.

Ruoslahti et al., "New Perspectives in Cell Adhesion: RGD and Integrins", Science, vol. 238, pp. 491–497 (1987).

*Primary Examiner*—Evelyn Huang
*Attorney, Agent, or Firm*—Richard S. Parr; Melvin Winokur

[57] ABSTRACT

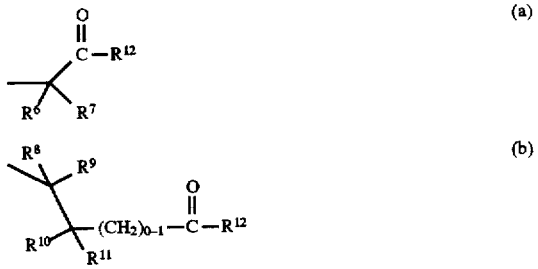

Novel fibrinogen receptor antagonists of the formula: X—Y—Z-Aryl-A—B and the pharmaceutically acceptable salts thereof, wherein Aryl is a 5-membered aromatic ring system containing 1 or 2 heteroatoms chosen from N, O or S wherein ring atoms may be unsubstituted or substituted with $R^5$ and wherein S may be substituted with 0, 1 or 2 oxygen atoms; and X comprises various Nitrogen substituents including aromatic or nonaromatic systems; Y comprises, for example, alkyl or alkylaminocarbonylalkyl groups and Z and A are substituents which when present are independently chosen from alkyl or alkyloxyalkyl or other groups as defined herein; B is (a) or (b). The claimed compounds exhibit fibrinogen receptor antagonist activity, inhibit platelet aggregation and are therefore useful in modulating or preventing thrombus formation.

13 Claims, No Drawings

FIBRINOGEN RECEPTOR ANTAGONISTS

This application is the National phase of PCT/US93/09750, filed Oct. 12, 1993, issued as WO 94/08577 on Apr. 28, 1994, which is a continuation of Ser. No. 07/960,977 filed Oct. 12, 1992, abandoned.

BACKGROUND OF THE INVENTION

The invention relates generally to modulating cell adhesion and to inhibiting the binding of fibrinogen and other proteins to blood platelets, and inhibiting the aggregation of blood platelets specifically to the IIb/IIIa fibrinogen receptor site. Fibrinogen is a glycoprotein present in blood plasma that participates in platelet aggregation and in fibrin formation. Platelets are cell-like anucleated fragments, found in the blood of all mammals, that also participate in blood coagulation. Interaction of fibrinogen with the IIb/IIIa receptor site is known to be essential for normal platelet function.

When a blood vessel is damaged by an injury or other causative factor, platelets adhere to the disrupted subendothelial surface. The adherent platelets subsequently release biologically active constituents and aggregate. Aggregation is initiated by the binding of agonists, such as thrombin, epinephrine, or ADP to specific platelet membrane receptors. Stimulation by agonists results in exposure of latent fibrinogen receptors on the platelet surface, and binding of fibrinogen to the glycoprotein IIb/IIIa (gp IIb/IIIa) receptor complex.

Attempts have been made to use natural products and synthetic peptides to determine the mechanism of adhesion and platelet aggregation. For example, Rouslahti and Pierschbacher in Science, 238, 491–497 (1987), describe adhesive proteins such as fibronectin, vitronectin, osteopontin, collagens, thrombospondin, fibrinogen, and von Willebrand factor that are present in extracellular matrices and in blood. The proteins contain the tripeptide segment arginine-glycine-aspartic acid ("RGD") as their glycoprotein IIb/IIIa recognition site. These arginine-glycine-aspartic acid containing tripeptides are recognized by at least one member of a family of structurally related receptors, integrins, which are heterodimeric proteins with two membrane-spanning subunits. The authors state that the conformation of the tripeptide sequence in the individual proteins may be critical to recognition specificity.

Cheresh in Proc. Nat'l Acad. Sci. U.S.A., 84, 6471–6475, (1987), describes an Arg-Gly-Asp directed adhesion receptor expressed by human endothethial cells that is structurally similar to the IIb/IIIa complex on platelets but is antigentically and functionally distinct. This receptor is directly involved in endothelial cell attachment to fibrinogen, von Willebrand factor, and vitronectin.

Pierschbacher and Rouslahti, in J. of Biol. Chem., 262, (36), 1729–17298 (1987) hypothesized that the Arg-Gly-Asp sequence alone would be a sufficient signal for receptor recognition and binding and that, therefore, the conformation of the tri-peptide sequence would be determinative. Various synthetic peptides were produced and the authors concluded that the conformation of Arg-Gly-Asp as influenced by enantiomeric substitutions or additions to this sequence significantly influenced receptor-ligand interaction. The authors further showed that cyclization of a decapeptide by forming a disulfide bridge between the non-terminal residues, Pen and Cys, rendered the peptide much less effective at inhibiting attachment to fibronectin.

In Proc. Nat'l Acad. Sci. U.S.A., 81, 5985–5988 (1984), the same authors describe tetrapeptide variants of the cell recognition site of fibronectin that retain attachment-promoting activity. Peptides having a tetrapeptide recognition site are described in U.S. Pat. Nos. 4,589,881 and 4,614,517. A number of large polypeptide fragments in the cell-binding domain of fibronectin have cell-attachment activity. For example, see U.S. Pat. Nos. 4,517,686 and 4,661,111.

Ruggeri et al., Proc. Nat'l Acad. Sci. U.S.A., 83, 5708–5712 (1986) explore a series of synthetic peptides designed in lengths to 16 residues, that contain RGD and a valine attached to the aspartic acid residue of RGD that inhibit fibrinogen binding to platelets. See also Koczewiak et al., Biochem. 23, 1767–1774 (1984); Ginsberg et al., J. Biol. Chem. 260(7), 3931–3936 (1985); and Haverstick et al., Blood 66(4), 946–952 (1985). Other inhibitors are disclosed in Eur. Pat. App. Nos. 275,748 and 298,820.

A number of low molecular weight polypeptide factors have been isolated from snake venom. These factors apparently have high affinity for the gpIIb/IIIa complex. For example, Huang et al., J. Biol Chem., 262, 16157–16163 (1987); Huang et al., Biochemistry 28, 661–666 (1989) describe the primary structure of the venom trigramin which is a 72 amino acid polypeptide that contains the RGD subunit. Echistatin is another venom which has high affinity for the gpIIb/IIIa complex. This polypeptide contains 49 amino acids and has the RGD subunit and various disulfide bridges. Gan et al., J. Biol. Chem., 263, 19827–19832 (1988). See also, Dennis et al., Proc. Nat'l Acad. Sci. U.S.A., 87, 2471–2475 (1989). However, these snake venom factors also have high affinity for other members of the adhesive protein receptor family including the vitronectin and fibronectin receptors and so are not selective for the gpIIb/IIIa complex.

While it is known that the tripeptide sequence Arg-Gly-Asp is present in certain polypeptides that can duplicate or inhibit the cell attachment-promoting effects of fibronectin and vitronectin, the tri-peptide Arg-Gly-Asp has low activity. At present, there is little understanding of how other amino acids coupled to this sequence influence binding specificity. U.S. Pat. No 5,023,233, assigned to Merck & Co., Inc., discloses small cyclic hexapeptides which contain the sequence Arg-Gly-Asp and are useful platelet aggregation inhibitors. U.S. Pat. No. 5,037,808 discloses the use of indolyl platelet-aggregation inhibitors which are believed to act by antagonizing interactions between fibrinogen and/or extracellular matrix proteins and the platelet gpIIb/IIIa receptor. U.S. Pat. No. 5,037,808 discloses guanidino peptide mimetic compounds that retain an Asp residue which inhibit platelet aggregation. The application PCT/US90/02746 describes the use of antibody-polypeptide conjugates wherein said polypeptides contain the Arg-Gly-Asp (RGD) sequence.

The application PCT/US91/00564 discloses the use of large cyclic peptides containing RGD flanked by proline residues which are platelet aggregation inhibitors. The application PCT/US90/03788 discloses small cyclic platelet aggregation inhibitors which are synthetic cyclic pentapeptides containing the tripeptide sequence Arg-Gly-Asp and a thioether linkage in the cycle. The application PCT/US90/05367 published May 2, 1991 also discloses the use of peptides and pseudopeptides such as N-amidinopiperidine-3-carboxylglycyl-L-aspartyl-L-valine that inhibit platelet aggregation and thrombus formation in mammalian blood. The application Eur. Pat. App. No. 91103462.7 discloses linear compounds which can include internal piperazinyl or piperidinyl derivatives. Eur. Pat. App. No. 91300179.8, assigned to Merck & Co., Inc., discloses long polypeptide fibrinogen receptor antagonists. Eur. Pat. App. No. 90101404.3 discloses compounds of the $R^1$—A—$(W)_a$—X—$(CH_2)_b$—$(Y)_c$—B—Z—COOR wherein $R^1$ is a guandidino or amidino moiety and A and B are chosen from specific monosubstituted aryl or heterocyclic moieties.

The present invention provides novel fibrinogen receptor antagonists that have fibrinogen receptor binding activity and are, therefore, useful for the reasons stated herein. A number of very serious diseases and disorders involve hyperthrombotic complications which lead to intravascular thrombi and emboli. Myocardial infarction, stroke, phlebitis and a number of other serious conditions create the need for novel and effective fibrinogen receptor antagonists.

SUMMARY OF THE INVENTION

The invention is a fibrinogen receptor antagonist of the formula:

X—Y—Z-Aryl-A—B and the pharmaceutically acceptable salts thereof wherein Aryl is a 5- or 6-membered aromatic ring system containing 1 or 2 heteroatoms chosen from N, O or S wherein ring atoms may be unsubstituted or substituted with $R^5$ and wherein S may be substituted with 0, 1 or 2 oxygen atoms; and X comprises:

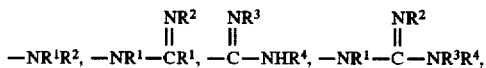

or a 5- to 6-membered mono- or bicyclic aromatic or nonaromatic ring system containing 0, 1 or 2 heteroatoms selected from N, O and S and either unsubstituted or substituted with $R^1$, $R^2$, $R^3$ or $R^4$, wherein $R^1$, $R^2$, $R^3$ and $R^4$ are independently selected from the group consisting of hydrogen,
$C_{1-10}$ alkyl,
aryl $C_{0-8}$ alkyl,
oxy,
thio,
amino $C_{0-8}$ alkyl,
$C_{1-3}$ acylamino $C_{0-8}$ alkyl,
$C_{1-6}$ alkylamino $C_{0-8}$ alkyl,
$C_{1-6}$ dialkylamino $C_{0-8}$ alkyl,
$C_{1-4}$ alkoxy $C_{0-6}$ alkyl,
carboxy $C_{0-6}$ alkyl,
$C_{1-4}$ alkoxycarbonyl $C_{0-6}$ alkyl,
carboxy $C_{0-6}$ alkyloxy or
hydroxy $C_{0-6}$ alkyl;

Y comprises:
$C_{0-8}$ alkyl,
$C_{4-10}$ cycloalkyl,
$C_{0-8}$ alkyl-$NR^3$-CO-$C_{0-8}$ alkyl,
$C_{0-8}$ alkyl-$CONR^3$-$C_{0-8}$ alkyl,
$C_{0-8}$ alkyl-O-$C_{0-8}$ alkyl,
$C_{0-8}$ alkyl-$S(O_n)$-$C_{0-8}$ alkyl,
$C_{0-8}$ alkyl-$SO_2$-$NR^3$-$C_{0-8}$ alkyl,
$C_{0-8}$ alkyl-$NR^3$-$SO_2$-$C_{0-8}$ alkyl,
$C_{0-8}$ alkyl-CO-$C_{0-8}$ alkyl,
$(CH_2)_{0-6}$ aryl$(CH_2)_{0-6}$,
$(CH_2)_{0-6}$aryl-CO-$(CH_2)_{0-6}$,
$C_{0-6}$ alkyl-aryl-$C_{0-6}$ alkyl,
$(CH_2)_{0-6}$aryl-CO-NH-$(CH_2)_{0-6}$,

$(CH_2)_{0-8}CH(CH_2)_{0-8}$

Z and A are independently chosen from:
$(CH_2)_m$, $(CH_2)_mO(CH_2)_n$, $(CH_2)_mNR^3(CH_2)_n$

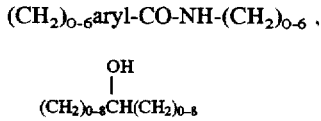

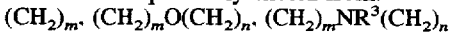

$(CH_2)_mSO_2(CH_2)_n$, $(CH_2)_mS(CH_2)_n$, $(CH_2)_mSO(CH_2)_n$, $(CH_2)_mSO_2NR^3(CH_2)_n$, $(CH_2)_mNR^3SO_2(CH_2)_n$, $(CH_2)_mCR^3=CR^4(CH_2)_n$, $(CH_2)_mC\equiv C-(CH_2)_n$.

where m and n are integers independently chosen from 0–6;

$R^5$ is
hydrogen,
hydroxyl,
$C_{1-6}$ alkyl,
$C_{0-6}$ alkylcarboxy $C_{0-6}$ alkyl,
$C_{0-6}$ alkyloxy $C_{0-6}$ alkyl,
hydroxy $C_{0-6}$ alkyl,
aryl $C_{0-6}$ alkyl, or
halogen;

B is

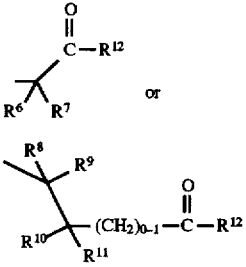

wherein:
$R^6$, $R^7$, $R^8$, $R^9$, $R^{10}$, and $R^{11}$ are independently chosen from:
hydrogen,
fluorine,
$C_{1-8}$ alkyl,
hydroxyl,
hydroxy $C_{1-6}$ alkyl,
carboxy $C_{0-6}$ alkyl,
$C_{1-6}$ alkyloxy,
aryl $C_{1-6}$ alkyloxy,
$C_{1-6}$ alkylcarbonyl $C_{0-6}$ alkyl,
aryl $C_{1-6}$ alkylcarbonyl $C_{0-6}$ alkyl,
$C_{1-6}$ alkylcarbonyloxy,
aryl $C_{0-6}$ alkylcarbonyloxy,
$C_{1-6}$ alkylaminocarbonyloxy,
aryl $C_{0-6}$ alkylaminocarbonyloxy,
$C_{3-8}$ cycloalkyl,
aryl $C_{0-6}$ alkyl,
$C_{0-6}$ alkylamino $C_{0-6}$ alkyl,
$C_{0-6}$ dialkylamino $C_{0-6}$ alkyl,
$C_{1-8}$ alkylsulfonylamino $C_{0-6}$ alkyl,
aryl $C_{0-6}$ alkylsulfonylamino $C_{0-6}$ alkyl,
$C_{1-8}$ alkyloxycarbonylamino $C_{0-8}$ alkyl, aryl $C_{0-8}$ alkyloxycarbonylamino $C_{0-8}$ alkyl,
$C_{1-8}$ alkylcarbonylamino $C_{0-6}$ alkyl,
aryl $C_{0-6}$ alkylcarbonylamino $C_{0-6}$ alkyl,
$C_{0-8}$ alkylaminocarbonylamino $C_{0-6}$ alkyl,
aryl $C_{0-8}$ alkylaminocarbonylamino $C_{0-6}$ alkyl,
$C_{0-8}$ alkylaminosulfonylamino $C_{0-6}$ alkyl,
aryl $C_{0-8}$ alkylaminosulfonylamino $C_{0-6}$ alkyl,
$C_{1-6}$ alkylsulfonyl $C_{0-6}$ alkyl,
aryl $C_{0-6}$ alkylsulfonyl $C_{0-6}$ alkyl,
$C_{1-6}$ alkylcarbonyl $C_{0-6}$ alkyl,
aryl $C_{0-6}$ alkylcarbonyl $C_{0-6}$ alkyl,
$C_{0-8}$ alkylaminosulfonyl $C_{0-8}$ alkyl,
aryl $C_{0-8}$ alkylaminosulfonyl $C_{0-8}$ alkyl,
$C_{0-8}$ alkylaminocarbonyl $C_{0-8}$ alkyl,
aryl $C_{0-8}$ alkylaminocarbonyl $C_{0-8}$ alkyl,
$C_{1-6}$ alkylthiocarbonylamino $C_{0-6}$ alkyl, or aryl $C_{0-6}$ alkylthiocarbonylamino $C_{0-6}$ alkyl wherein the alkyl or aryl groups may be unsubstituted or substituted with one or more substituents selected from $R^1$ and $R^2$;

$R^{12}$ is chosen from
hydroxy,
$C_{1-8}$ alkyloxy,
aryl $C_{0-6}$ alkyloxy,
$C_{1-8}$ alkylcarbonyloxy $C_{1-4}$ alkyloxy,
aryl $C_{1-8}$ alkylcarbonyloxy $C_{1-4}$ alkyloxy, or an L- or D-amino acid joined by an amide linkage and wherein the carboxylic acid moiety of said amino acid is as the free acid or is esterified by $C_{1-6}$ alkyl;

A preferred embodiment of the present invention is

X—Y—Z-Aryl-A—B and the pharmaceutically acceptable salts thereof, wherein Aryl is a 5- or 6-membered aromatic ring system containing 1 or 2 heteroatoms chosen from N, O or S wherein ring atoms may be unsubstituted or substituted with $R^5$ and wherein S may be substituted with 0, 1 or 2 oxygen atoms;

X comprises:

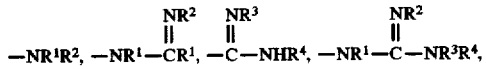

or a 5- to 6-membered mono- or bicyclic aromatic or nonaromatic ring system containing 0, 1, 2, 3 or 4 heteroatoms selected from N, O and S and either unsubstituted or substituted with $R^1$, $R^2$, $R^3$ or $R^4$, wherein $R^1$, $R^2$, $R^3$ and $R^4$ are independently selected from the group consisting of hydrogen,
$C_{1-10}$ alkyl,
aryl $C_{0-8}$ alkyl,
amino $C_{0-8}$ alkyl,
$C_{1-3}$ acylamino $C_{0-8}$ alkyl,
$C_{1-6}$ alkylamino $C_{0-8}$ alkyl,
$C_{1-6}$ dialkylamino $C_{0-8}$ alkyl,
$C_{1-4}$ alkyloxy $C_{0-6}$ alkyl,
carboxy $C_{0-6}$ alkyl,
$C_{1-4}$ alkyloxycarbonyl $C_{0-6}$ alkyl,
carboxy $C_{0-6}$ alkyloxy or
hydroxy $C_{0-6}$ alkyl;

Y is
$C_{0-8}$ alkyl,
$C_{0-8}$ alkyl-$NR^3$-CO-$C_{0-8}$ alkyl,
$C_{0-8}$ alkyl-$CONR^3$-$C_{0-8}$ alkyl,
$C_{0-8}$ alkyl-O-$C_{0-8}$ alkyl,
$C_{0-8}$ alkyl-S(O$_n$)-$C_{0-8}$ alkyl,
$C_{0-8}$ alkyl-SO$_2$-$NR^3$-$C_{0-8}$ alkyl-, or
$C_{0-6}$ alkyl-aryl-$C_{0-6}$ alkyl;

Z and A are independently chosen from
$(CH_2)_m$, $(CH_2)_mO(CH_2)_n$,

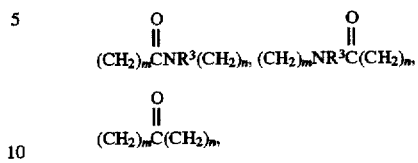

$(CH_2)_mSO_2(CH_2)_n$,
$(CH_2)_mSO_2NR^3(CH_2)_n$, or $(CH_2)_mNR^3SO_2(CH_2)_n$;
where m and n are integers independently chosen from 0–6;

B is

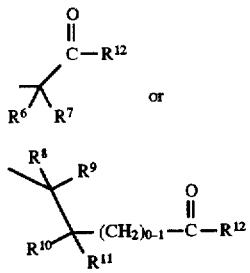

wherein $R^6$, $R^7$, $R^8$, $R^9$, $R^{10}$ and $R^{11}$ are independently chosen from
hydrogen,
fluorine,
$C_{1-8}$ alkyl,
$C_{3-8}$ cycloalkyl,
aryl $C_{0-6}$ alkyl,
$C_{0-6}$ alkylamino $C_{0-6}$ alkyl,
$C_{0-6}$ dialkylamino $C_{0-6}$ alkyl,
$C_{1-8}$ alkylsulfonylamino $C_{0-6}$ alkyl,
aryl $C_{0-6}$ alkylsulfonylamino $C_{0-6}$ alkyl,
$C_{1-8}$ alkyloxycarbonylamino $C_{0-8}$ alkyl,
aryl $C_{0-8}$ alkyloxycarbonylamino $C_{0-8}$ alkyl,
$C_{1-8}$ alkylcarbonylamino $C_{0-6}$ alkyl,
aryl $C_{0-6}$ alkylcarbonylamino $C_{0-6}$ alkyl,
$C_{0-8}$ alkylaminocarbonylamino $C_{0-6}$ alkyl,
aryl $C_{0-8}$ alkylaminocarbonylamino $C_{0-6}$ alkyl,
$C_{0-8}$ alkylaminosulfonylamino $C_{0-6}$ alkyl,
aryl $C_{0-8}$ alkylaminosulfonylamino $C_{0-6}$ alkyl,
$C_{1-6}$ alkylsulfonyl $C_{0-6}$ alkyl,
aryl $C_{0-6}$ alkylsulfonyl $C_{0-6}$ alkyl,
$C_{1-6}$ alkylcarbonyl $C_{0-6}$ alkyl, or
aryl $C_{0-6}$ alkylcarbonyl $C_{0-6}$ alkyl, $R^{12}$ is chosen from
hydroxy,
$C_{1-8}$ alkyloxy,
aryl $C_{0-6}$ alkyloxy,
$C_{1-8}$ alkylcarbonyloxy $C_{1-4}$ alkyloxy, or
aryl $C_{1-8}$ alkylcarbonyloxy $C_{1-4}$ alkyloxy, A more preferred embodiment of the present invention is

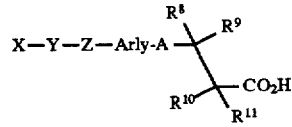

and the pharmaceutically acceptable salts thereof, wherein Aryl is a 5-membered aromatic ring system containing 1 or 2 heteroatoms chosen from N, O or S wherein ring atoms may be unsubstituted or substituted with $R^5$ and wherein S may be substituted with 0, 1 or 2 oxygen atoms;

X is

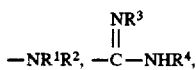

or a 5- to 6-membered nonaromatic ring system containing 0, 1 or 2 heteroatoms selected from N and O wherein $R^1$, $R^2$, $R^3$ or $R^4$, are independently selected from the group consisting of hydrogen,
$C_{1-10}$ alkyl,
aryl $C_{0-8}$ alkyl,
carboxy $C_{0-6}$ alkyl,
hydroxy $C_{0-6}$ alkyl,
amino $C_{0-8}$ alkyl, or
$C_{1-6}$ alkylamino $C_{0-8}$ alkyl;

Y is
$C_{0-8}$ alkyl,
$C_{0-8}$ alkyl-$NR^3$-CO-$C_{0-8}$ alkyl,
$C_{0-8}$ alkyl-$CONR^3$-$C_{0-8}$ alkyl,
$C_{0-8}$ alkyl-O-$C_{0-8}$ alkyl, or
$C_{0-8}$ alkyl-$S(O_n)$-$C_{0-8}$ alkyl;
where n is 0–2;

Z and A are independently chosen from
$(CH_2)_m$,

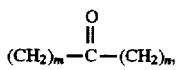

$(CH_2)_m$—O—$(CH_2)_n$,
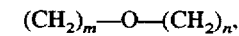$(CH_2)_m SO_2$—$(CH_2)_n$, $(CH_2)_m CONH$—$(CH_2)_n$,
wherein m and n are integers independently chosen from 0–6;

$R^8$, $R^9$, $R^{10}$ and $R^{11}$ are independently chosen from
hydrogen,
fluorine,
$C_{1-8}$ alkyl,
$C_{3-8}$ cycloalkyl,
aryl $C_{0-6}$ alkyl,
$C_{0-6}$ alkylamino $C_{0-6}$ alkyl,
$C_{0-6}$ dialkylamino $C_{0-6}$ alkyl,
$C_{1-8}$ alkylsulfonylamino $C_{0-6}$ alkyl,
aryl $C_{0-6}$ alkylsulfonylamino $C_{0-6}$ alkyl,
$C_{1-8}$ alkyloxycarbonylamino $C_{0-8}$ alkyl,
aryl $C_{0-8}$ alkyloxycarbonylamino $C_{0-8}$ alkyl,
$C_{1-8}$ alkylcarbonylamino $C_{0-6}$ alkyl,
aryl $C_{0-6}$ alkylcarbonylamino $C_{0-6}$ alkyl,
$C_{0-8}$ alkylaminocarbonylamino $C_{0-6}$ alkyl,
aryl $C_{0-8}$ alkylaminocarbonylamino $C_{0-6}$ alkyl,
$C_{0-8}$ alkylaminosulfonylamino $C_{0-6}$ alkyl,
aryl $C_{0-8}$ alkylaminosulfonylamino $C_{0-6}$ alkyl,
$C_{1-6}$ alkylsulfonyl $C_{0-6}$ alkyl,
aryl $C_{0-6}$ alkylsulfonyl $C_{0-6}$ alkyl,
$C_{1-6}$ alkylcarbonyl $C_{0-6}$ alkyl, or
aryl $C_{0-6}$ alkylcarbonyl $C_{0-6}$ alkyl.

The most preferred compounds of the present invention are:
3-{5-[5-(4-Piperidinyl)pentyl}thien-2-yl-2-(N-benzyloxycarbonylamino)-propanoic acid,
N-2-(4-Piperidinyl)ethyl-N'-3-[2(S)-n-butylsulfonylaminopropanoic acid]-2,5-thiophenedicarboxamide,
N-2-(4-Piperidinyl)ethyl-N'-(2-carboxyethyl)-2,5-thiophenedicarboxamide,
3-[3-(Piperidin-yl)propyloxy]isoxazole-5-carbonyl-2(S)-butylsulfonylamino-β-alanine,
3-[4-(Piperidin-4-yl)butyloxy]isoxazole-5-carbonyl-2(S)-phenylsulfamoylamino-β-alanine,
3-[2-(Piperidin-4-yl)ethylloxy]isoxazole-5-carbonyl-2(S)-phenylsulfonylamino-β-alanine,
2-[2-(Piperidin-4-yl)ethylthio]imidazole-4-carbonyl-2(S)-phenylsulfonylamino-β-alanine,
2-[3-(Piperidin-4-yl)propylthio]thiophene-5-carbonyl-2(S)-phenylsulfonylamino-β-alanine,
5-[(2-N,N-Diethylaminoethyl)oxymethyl]thiophene-2-carbonyl-2(S)-phenylsulfonylamino-β-alanine methyl ester,
5-[(2-N,N-Diethylaminoethyl)oxymethyl]thiophene-2-carbonyl-2(S)-phenylsulfonylamino-β-alanine,
5-(4-Pyridylmethyloxymethyl)thiophene-2-carbonyl-2(S)-phenylsulfonylamino-β-alanine methyl ester,
5-(4-Pyridylmethyloxymethyl)thiophene-2-carbonyl-2(S)-phenylsulfonylamino-β-alanine, and
2-[3-(Piperidin-4-yl)propyl-1-sulfonyl]thiophene-5-carbonyl-2(S)-phenylsulfonylamino-β-alanine.

DETAILED DESCRIPTION OF THE INVENTION

The term "pharmaceutically acceptable salts" means nontoxic salts of the compounds of this invention which are generally prepared by reacting the free base with a suitable organic or inorganic acid. Representative salts include the following salts: Acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, glucoheptanate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, pantothenate, phosphate/diphosphate, polygalactouronate, salicylate, stearate, subacetate, succinate, tannate, tartrate, teoclate, tosylate, triethiodide, valerate.

The term "pharmaceutically effective amount" means that amount of a drug or pharmaceutical agent that will elicit the biological or medical response of a tissue, system or animal that is being sought by a researcher or clinician. The term "anti-coagulant" includes, for example, heparin and warfarin. The term "thrombolytic agent" includes, for example, streptokinase, urokinase and tissue plasminogen activator. The term "platelet anti-aggregation agent" includes, for example, aspirin and dipyridamole.

The term "aryl," to be distinguished from the previously defined term "Aryl," means a mono- or bicyclic system composed of 5- and/or 6-membered aromatic rings containing 0, 1 or 2 heteroatoms chosen from N, O or S and either unsubstituted or substituted. "aryl" with a lower case "a" is defined herein to be broader than the term "Aryl" with a capital "A". One skilled in the art can readily distinguish between the two terms which are clearly defined herein.

The term "alkyl" means straight or branched alkane, alkene or alkyne.

The term "alkoxy" includes an alkyl portion where alkyl is as defined above.

The terms "arylalkyl" and "alkylaryl" include an alkyl portion where alkyl is as defined above and to include an aryl portion where aryl is as defined above. The $C_{0-n}$ or $C_{1-n}$ designation where n may be an integer from 1–10 or 2–10 respectively, refers to the alkyl component of the arylalkyl or alkylaryl unit.

The term "halogen" includes fluorine, chlorine, iodine and bromine. The term "oxy" means an oxygen (O) atom. The term "oxo" refers to a bivalent oxygen atom (=O). The term "thio" means a sulfur (S) atom.

Under standard nonmenclature used throughout this disclosure, the terminal portion of the designated side chain is described first followed by the adjacent functionallity toward the point of attachment. For example, a $C_{1-6}$ alkyl substituted with $C_{1-6}$ alkylcarbonylamino is equivalent to

In the schemes and examples below, various reagent symbols have the following meanings:
BOC(Boc): t-butyloxycarbonyl.
Pd/C: Palladium on activated carbon catalyst.
DMF: Dimethylformamide.
DMSO: Dimethylsulfoxide.
CBZ(CBz): Carbobenzyloxy or benzyloxycarbonyl.
$CH_2Cl_2$: Methylene chloride.
$CHCl_3$: Chloroform.
EtOH: Ethanol.
NMM: N-methylmorpholine
NaHMDS: Sodium hexamethyldisilazane
CDI: Carbonyldiimidazole
HOBT: 1-Hydroxybenzotriazole
MeOH: Methanol.
EtOAc: Ethyl acetate.
HOAc: Acetic acid.
BOP: Benzotriazol-1-yloxytris(dimethylamino) phosphonium hexafluorophosphate.
EDC: 1-(3-Dimethylaminopropyl)-3-ethylcarbodiimide
Oxone: potassium peroxymonosulfate
LDA: Lithium diisopropylamide
THF: Tetrahydrofuran
TEA: Triethylamine
TFA: Trifluoroacetic acid
DIEA: Diisopropylethylamine The compounds of the present invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramusculsar form, all using forms well known to those of ordinary skill in the pharmaceutical arts. An effective but non-toxic amount of the compound desired can be employed as an anti-aggregation agent.

Compounds of the invention may be administered to patients where prevention of thrombosis by inhibiting binding of fibrinogen to the platelet membrane glycoprotein complex IIb/IIIa receptor is desired. They are useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. They may be administered to these surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between gpIIb/IIIa on the platelet membranes and fibrinogen adsorbed to the surface of the circuit. (Gluszko et al., Amer. J. Physiol., 252(H), 615–621(1987)). Platelets released from artificial surfaces show impaired hemostatic function. Compounds of the invention may be administered to prevent adhesion.

Other applications of these compounds include prevention of platelet thrombosis, thromboembolism and reocclusion during and after thrombolytic therapy and prevention of platelet thrombosis, thromboembolism and reocclusion after angioplasty or coronary artery bypass procedures. They may also be used to prevent myocardial infarction.

The dosage regimen utilizing the compounds of the present invention is selected in accordance with a variety of factors including type, species, age, weight, sex and medical condition of the patient; the severity of the condition to be treated; the route of adminstration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the present invention, when used for the indicated effects, will range between about 0.01 mg per kg of body weight per day (mg/kg/day) to about 100 mg/kg/day and preferably 0.1–100 mg/kg/day and most preferably 1–20 mg/kg/day. Intravenously, the most prefered doses will range from about 1 to about 10 µ/kg/minute during a constant rate infusion. Advantageously, compounds of the present invention may be administered in divided doses of two, three, or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather that intermittant throughout the dosage regime.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium sterate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium sterate, magnesium sterate, sodium benzoate, sodium acetate, sodium chloride and the like. Disintegrators include, without limitation, starch methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include poly-vinlypyrrolidone, pyran copolymer, polyhydroxypropyl-methacrylamide-phenol, polyhydroxyethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The compounds of the present invention can also be co-administered with suitable anti-coagulation agents or thrombolytic agents such as plasminogen activators or streptokinase to achieve synergystic effects in the treatment of various vascular pathologies. They may also be combined with heparin, aspirin, or warfarin.

The novel compounds of the present invention were prepared according to the procedure of the following schemes and examples, using appropriate materials and are further exemplified by the following specific examples. The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted.

In addition to the following preparative procedures, an example of in-vitro bioactivity of compounds within the scope of the present invention is indicated. To illustrate, one test which is used to evaluate fibrinogen receptor antagonist activity is based on evaluation of inhibition of the aggregation of ADP-stimulated platelets. Aggregation requires that fibrinogen bind to and occupy the platelet fibrinogen receptor site. Inhibitors of fibrinogen binding inhibit aggregation. In the ADP-stimulated platelet aggregation assay used to determine inhibition associated with the compounds claimed in the instant invention, human platelets are isolated from fresh blood, collected into acid citrate/dextrose by differential centrifugation followed by gel filtration on Sepharose 2B in divalent ion-free Tyrode's buffer (pH 7.4) containing 2% bovine serum albumin.

Platelet aggregation is measured at 37° C. in a Chronolog aggregometer. The reaction mixture contains gel-filtered human platelets ($2\times10^8$ per ml), fibrinogen (100 micrograms per ml (ug/ml)), $Ca^{2+}$ (1 mM), and the compound to be tested. The aggregation is initiated by adding 10 mM ADP 1 minute after the other components are added. The reaction is then allowed to proceed for at least 2 minutes. The extent of inhibition of aggregation is expressed as the percentage of the rate of aggregation observed in the absence of inhibitor. The $IC_{50}$ is the dose of a particular compound inhibiting aggregation by 50% relative to a control lacking the compound.

Synthesis of Novel Fibrinogen Receptor Antagonists

Compounds useful as fibrinogen receptor antagonists may be prepared according to the general scheme depicted in Scheme 1.

In general terms, the intermediate thiophene compound 1-6 possessing the desired protected S-amino acid and a 5-bromo substituent for coupling is prepared by first alkylating the S-isomer of the Seebach chiral glycine equivalent 1-1 with a halomethyl compound 1-2 using lithium diisopropylamide (LDA) to generate the enolate. This reaction generates the coupled product 1-3 which is then deprotected with trifluroacetic acid (TFA) to yield 1-4. The amino acid is unmasked by hydrolysis to give the bromothiophene amino acid 1-5. The protected moiety 1-6 is obtained after methylation of the carboxyl group to form the methyl ester followed by treatment with benzyloxycarbonyl chloride.

A 4-piperidinylpentyl side chain is constructed using the aldehyde 1-7 and the TMS protected alkyne 1-8. The ylide generated from 1-8 is condensed with the aldehyde 1-7 to give the trans olefin 1-9. The TMS group is then removed with lithium hydroxide to give the alkyne 1-10. This moiety is then coupled to the protected thiophene amino acid 1-6 using a triphenylphosphine palladium chloride complex, copper iodide, and diethylamine to yield 1-11. This enyne moiety may then be reduced with hydrogen/palladium-on-carbon to yield 1-12. The Boc-protecting group on the piperidine substituent and the methyl group of the methyl ester are subsequently removed with HCl•EtOAc and LiOH•H₂O, respectively to give 1-13.

SCHEME 1

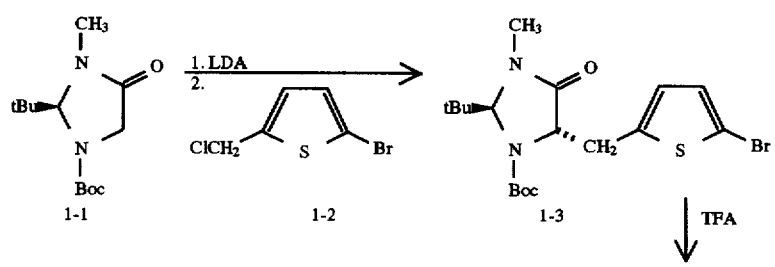

13

-continued
SCHEME 1

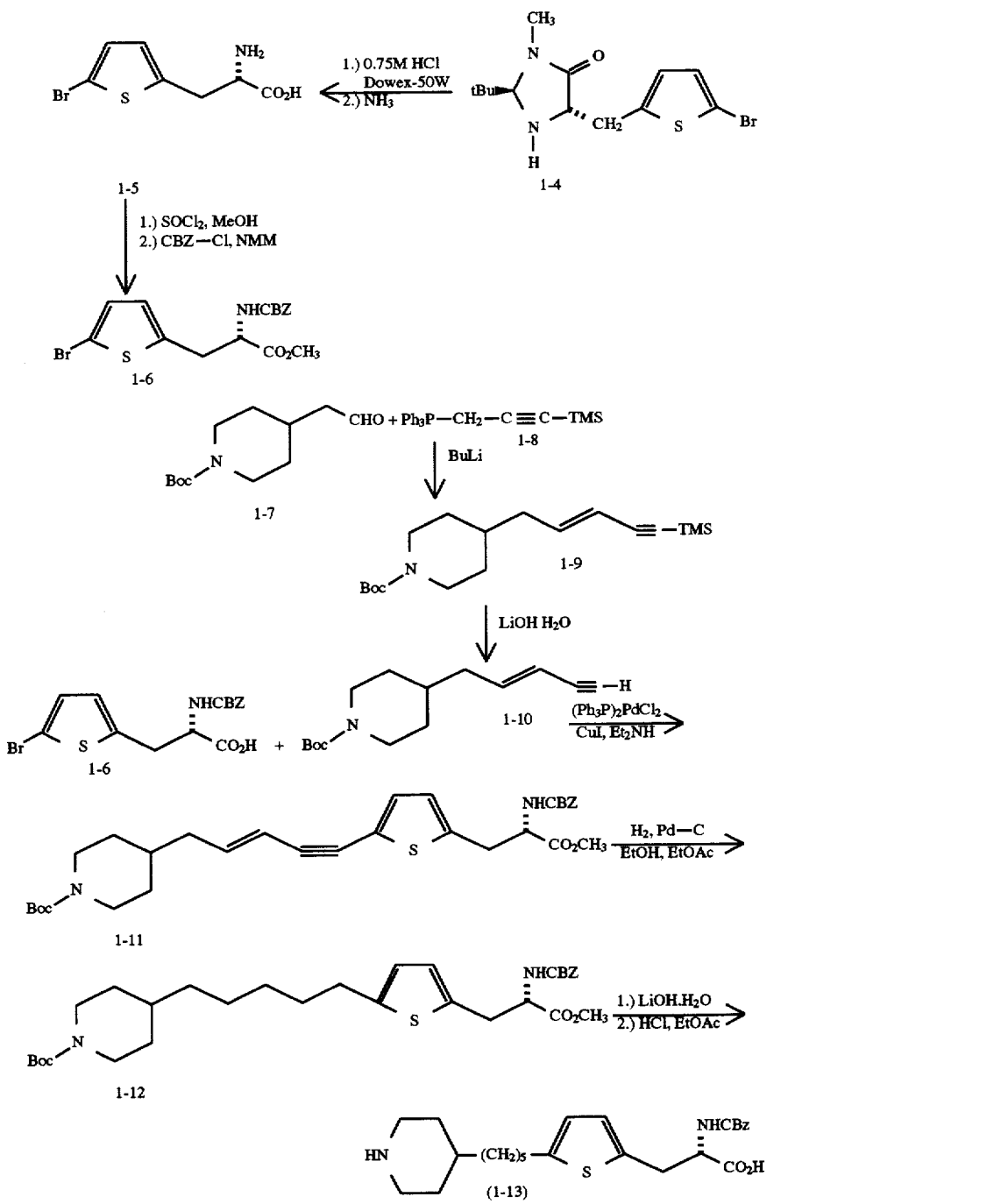

Compounds claimed in the instant invention and depicted in the following formula:

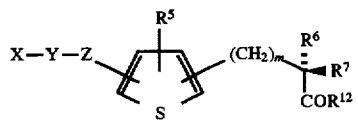
(I)

can readily be prepared according to this general scheme by substituting or replacing the various reagents in Scheme 1. When Z is a $C_{0-10}$alkyl or cycloalkyl, an analogous Wittig reaction to that depicted in Scheme 1 may be performed in which 1-7 is replaced by another heterocyclic or aromatic aldehyde chosen from, for example,

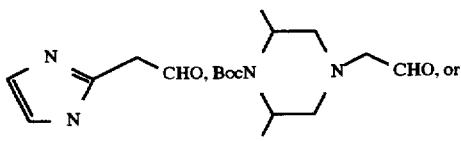

-continued

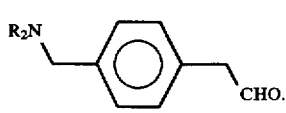

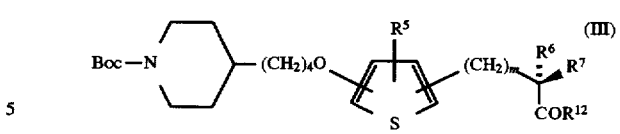

The thiophene compound 1-6 or, alternatively, a compound of the general formula:

Compounds of the invention may also be prepared according to Scheme 2.

SCHEME 2

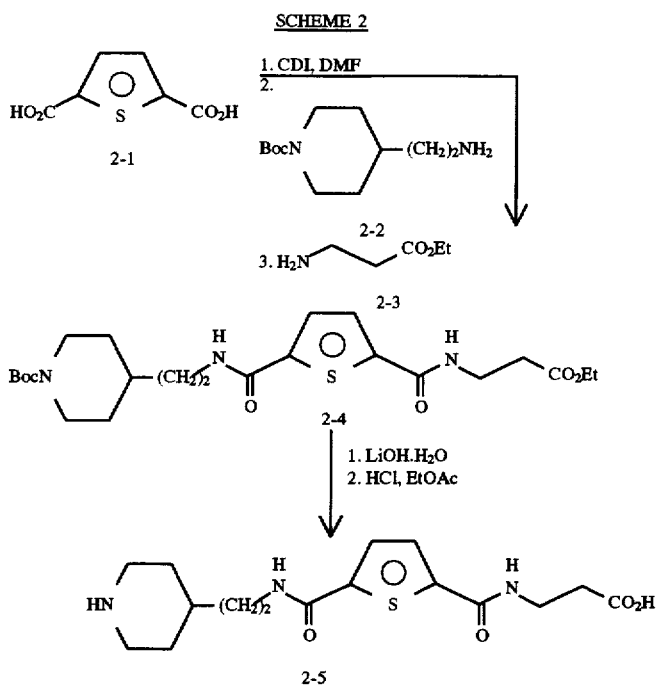

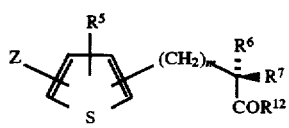

wherein Z is OH; $R^6$ or $R^7$ is chosen from $C_{0-10}$ alkyl, aryl $C_{1-10}$alkyl, halogen, $C_{1-6}$ alkylsulfonyl$C_{0-6}$alkyl, aryl$C_{1-10}$alkylsulfonyl$C_{0-6}$alkyl, $C_{0-6}$ alkylaminosulfonyl-$C_{0-6}$alkyl, $C_{0-6}$ alkylamino-carbonyl$C_{0-6}$alkyl, $C_{1-6}$ alkylsulfonylamino-$C_{0-6}$alkyl, aryl$C_{1-10}$ alkylsulfonylamino-$C_{0-6}$alkyl, $C_{1-6}$ alkylcarbonylamino$C_{0-6}$alkyl, aryl$C_{1-10}$alkylcarbonylamino$C_{0-6}$ alkyl, $C_{1-6}$alkyloxycarbonylamino$C_{0-6}$alkyl, or aryl $C_{1-10}$alkyloxycarbonylamino$C_{0-6}$alkyl; $R^{12}$ is hydroxy, $C_{1-8}$ alkyloxy, aryl $C_{0-6}$alkyloxy, $C_{1-8}$ alkylcarbonyloxy$C_{1-4}$alkyloxy or an L- or D-amino acid joined by an amide linkage and wherein the carboxylic acid moiety of said amino acid is as the free acid or is esterified by $C_{1-6}$ alkyl, may be prepared by known synthetic methodology, reacted with sodium hydride and 4-(4-N-t-butyloxycarbonylpiperidinyl)butyl bromide or other suitable alkyl or arylalkyl halide to yield:

As Scheme 2 illustrates, an Aryldicarboxylic acid derivative of the formula depicted below may be reacted with a suitably protected X group as defined herein and with an amino ester as defined herein to provide compounds within the scope of the instant invention:

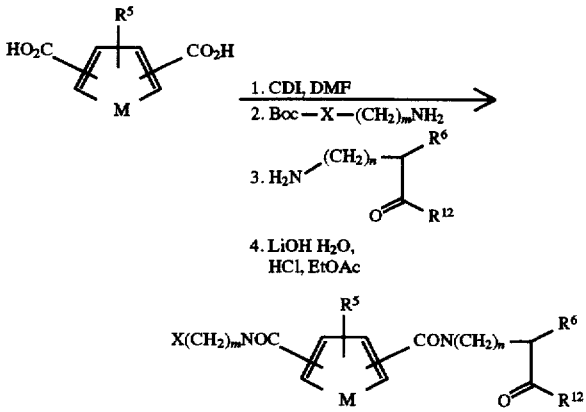

M is defined as N, O or S, where m and n are independently chosen from 0–6. Scheme 2 (con't) further depicts how compounds within the scope of the instant invention may be prepared.

SCHEME 2
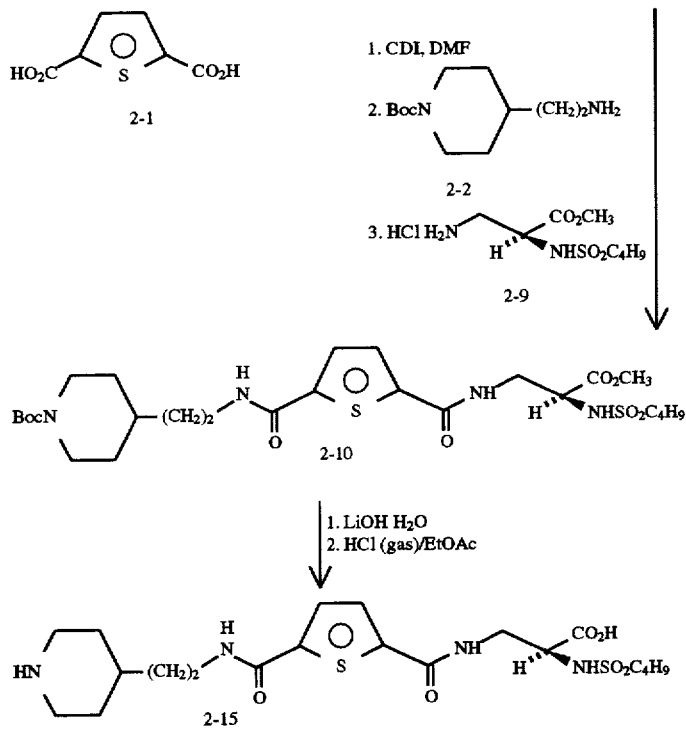
SCHEME 3
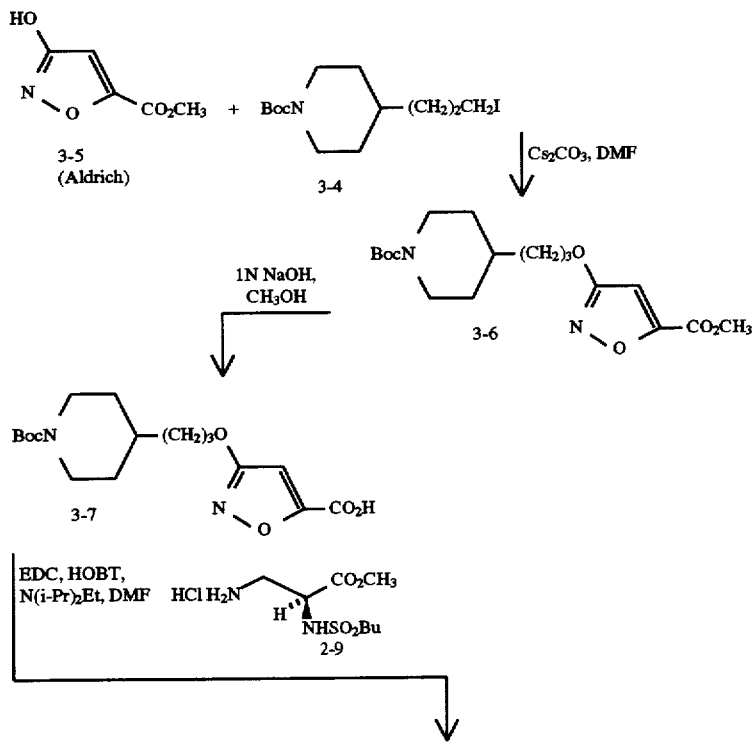

-continued
SCHEME 3

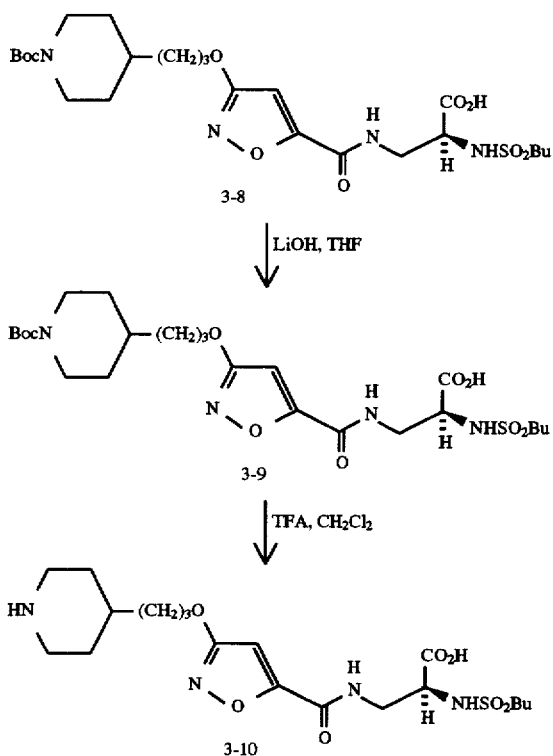

Scheme 3 provides an alternative method of producing compounds claimed in the instant invention. In general, a suitably substituted Aryl group as defined herein is reacted with Boc-X-(CH$_2$)m-halogen, hydrolyzed to the corresponding acid, and further derivatized with an amine to form compounds within the scope of the instant invention. Schemes 4 and 5 further illustrate the synthesis of compounds within the scope of the claimed invention. The compounds are active as fibrinogen receptor antagonists.

SCHEME 4

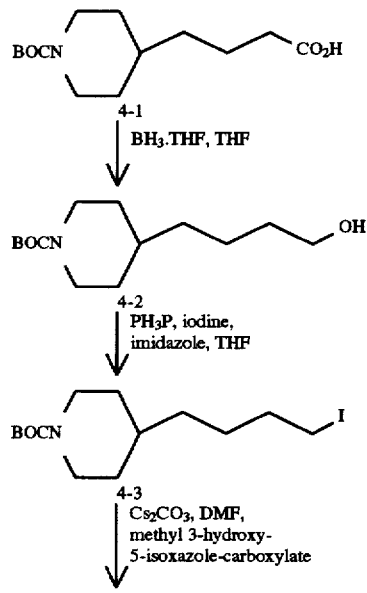

-continued
SCHEME 4
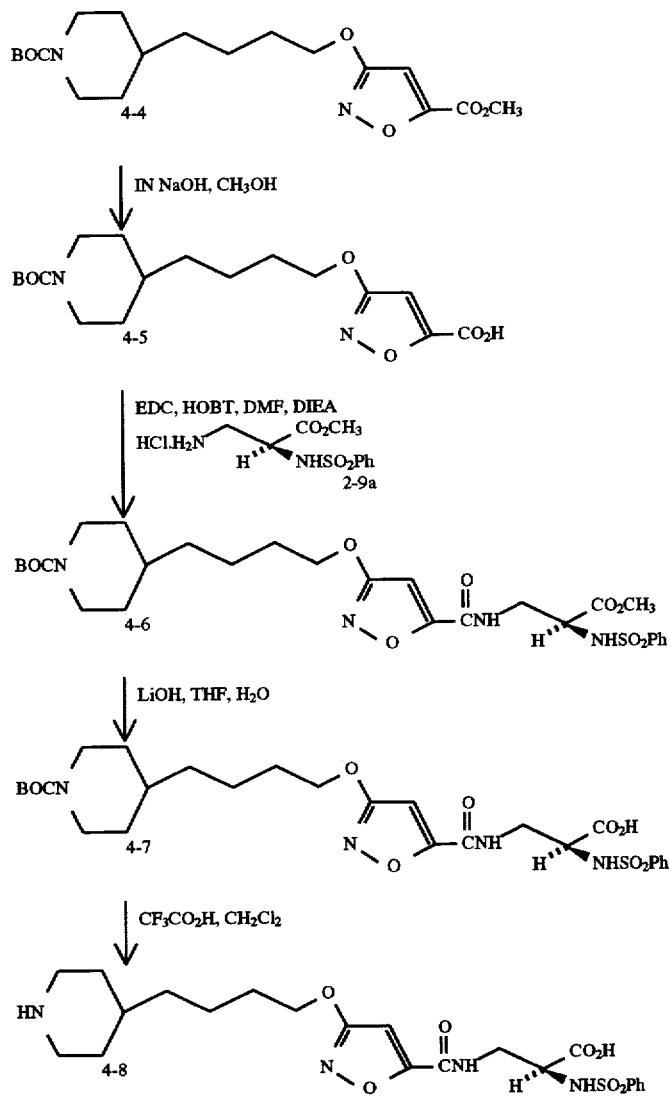
SCHEME 5
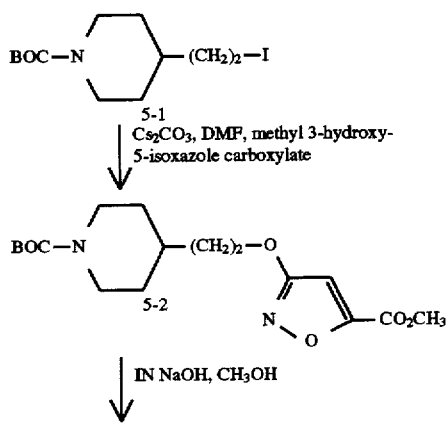
-continued
SCHEME 5
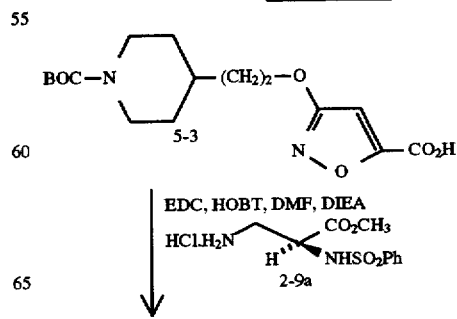

SCHEME 5
-continued
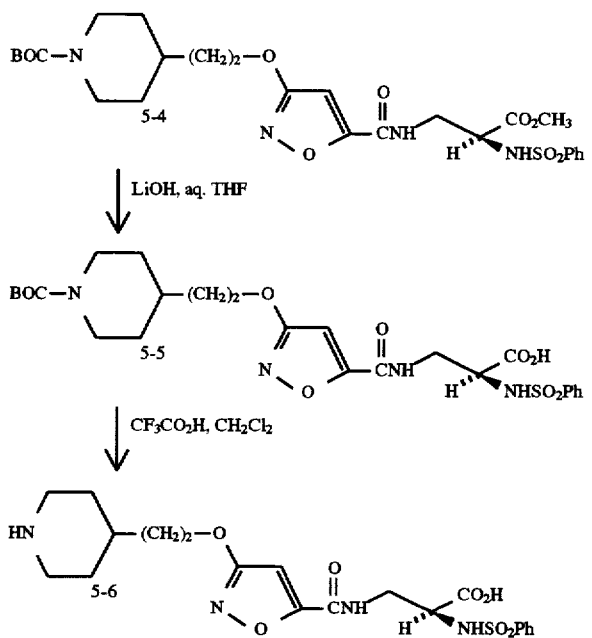
SCHEME 6
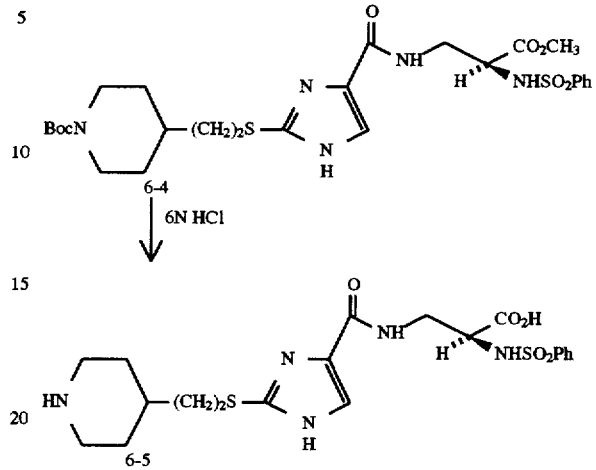
SCHEME 7

SCHEME 7 -continued

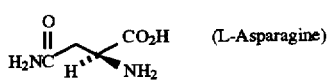

(L-Asparagine)

7-7 | NaOH, H₂O
     | PhSO₂Cl

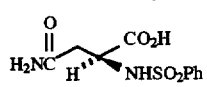

7-8

NaOH, dioxane, Br₂
0° to 90°

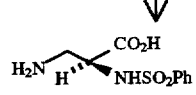

7-9

H₂SO₄, dioxane
isobutylene

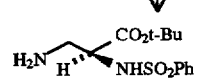

7-4

SCHEME 8

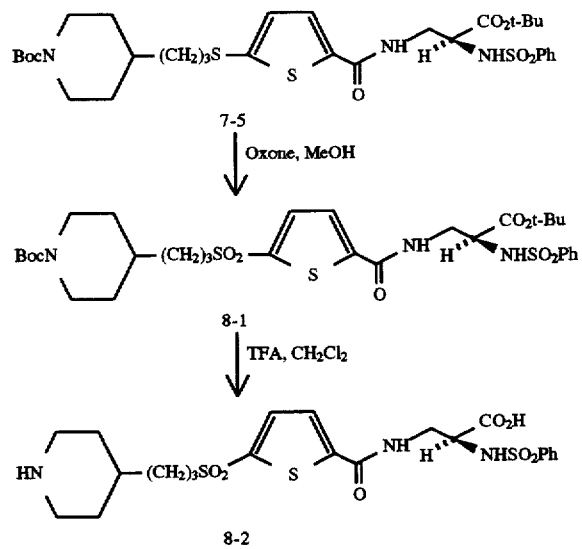

The following examples further describe the claimed invention. Compounds within the scope of the instant invention are prepared from readily available starting materials and may be prepared according to the Schemes or examples contained herein.

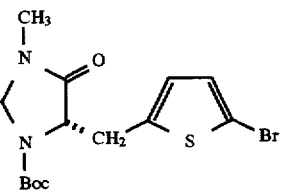

t-Butyl (2S,5S)-2-(t-Butyl)-3-methyl-4-oxo-5-[2-(5-bromothienylmethyl]-1-imidazolidenocarboxylate (1-3)

A solution of 1-1 (2.56 g, 10 mmol) was dissolved in THF (25 ml) and added dropwise to a 78° C. solution of LDA (11 mmol) in THF (30 ml), cooled to −78°, and the resulting mixture was stirred at −78° for 90 min. Then, 1-2(2.33 g, 11 mmol) in THF (15 ml) was added at −78° and the reaction mixture was stirred at −780° for 6 hrs.

The reaction mixture was diluted with ether (100 ml), and $H_2O$ (100 ml), saturated $NH_4Cl$ solution (10 ml), and the organic phase was separated, washed with brine and dried ($MgSO_4$). Solvent removal gave a residue that was purified by flash chromatography on silica gel eluting in hexane (7)/EtOAc (3) to give pure 1-3.

$^1$H NMR (300 MHz, $CDCl_3$) δ 0.95 (9H, s), 1.49 (9H,s), 3.00 (3H,s), 3.80 (1H, d), 4.22 (1H, bs), 6.57 (1H, bs), 6.77 (1H, bs).

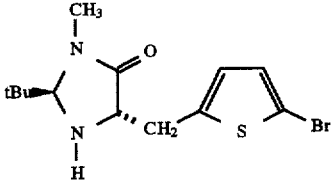

2-t-Butyl-3-methyl-4-oxo-5-S-[2-(5-bromothienylmethyl] imidazolidinone (1-4)

A solution of 1-3 (2.18 g, 5.2 mmol) in $CH_2Cl_2$ (10 ml) was treated at 0° with TFA (6.0 g, 52 mmol) and this reaction mixture was allowed to stir at room temperature for 20 hrs. Then the solvent was removed to provide 1-4 as an oil.

$^1$H NMR (300 MHz, $CDCl_3$) δ 1.11 (9H,s), 3.00 (3H, s), 3.55 (4H, m), 4.35 (2H, t), 4.55 (2H, s), 6.72 (2H, d), 6.89 (2H, d).

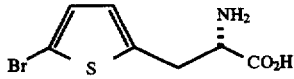

3-[2'-(5-bromothienyl)]-2(S)-aminopropanoic acid (1-5)

A solution of 1-4 in 0.75M HCl was swirled at room temperature for 0.5 hr. Then, Dowex-SOW resin was added along with toluene (10 ml) and the resulting suspension was stirred and heated at 100° for 48 hrs. This mixture was then poured into a column and eluted with $CH_3CN(4)/MeOH(1)/H_2O(1)$. This filtrate was stripped to dryness and the residue was dissolved in $H_2O$ and this solution placed on the Dowex column and eluted with ethanol and then $H_2O$ until the filtrate was neutral. This column was then eluted with 10% $NH_4OH$ to provide 1-5.

$^1$H NMR (300 MHz, $CD_3OD+D_2O$) δ 3.26–3.45 (6H, m), 3.89 (2H, m), 6.81 (2H, d), 7.02 (2H, d).

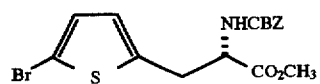

Methyl 3-[2'-(5-bromothienyl)]-2(S)-[N-benzyloxycarbonylamino]propanoate (1-6)

A suspension of 1-5 (0.93 g, 3.72 mmol) in MeOH (35 ml) was cooled to -5° C and treated with SOCl₂ (6.64 g, 55.8 mmol) dropwise. This was then stirred at -5° for 1.5 hr and then at 40° for 16 hours.

The solvent was then removed and the residue triturated with Et₂O to give the desired ester. R$_f$ 0.81 (Silica gel, CH₃CN(1)/MeOH(1)/-H₂O(1).) ¹H NMR (300 MHz, CD₃OD)δ3.30 (1H, m), 3.41 (2H, m), 3.85 (3H, s), 4.35 (1H, m), 6.78 (1H, d), 7.00 (1H, d).

This ester (1.06 g, 3.53 mmol) was suspended in CH₂Cl₂ (20 ml) cooled to 10°, CBZ chloride (0.66 g, 3.85 mmole) was added followed by N-methylmorpholine (0.39 g, 3.85 mmole). This was stirred for 2 hours and then diluted with ether (150 ml) and 10% citric acid solution (50 ml). The organic phase was separated, washed with saturated NaHCO₃ solution, brine and dried (MgSO₄). Solvent removal gave a residue that was purified by flash chromatography on silica gel eluting with hexane(2)/EtOAc(1) to give 1-6 as an oil. ¹H NMR (300 MHz, CDCl₃) δ3.30 (2H, m), 3.83 (3H, s), 4.62 (1H, m), 5.10 (2H, s), 5.39 (1H, d), 6.51 (1H, d), 6.83 (1H, d), 7.33 (5H, m).

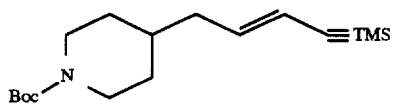

1-9

5-[4-(N-Boc-Piperidin-4-yl)]-1-trimethylsilylpent-3-ene-1-yne (1-9)

A suspenison of (1-8) (3.17 g, 7.0 mmol) in THF (20 ml) was cooled to −78° and treated with n-butyllithium (7.0 mmol) dropwise with stirring for 0.5 hr. This solution was stirred at −50° C. for 0.5 hr. Then, 4-(N-Boc-piperidin-4-yl)acetaldehyde (1-7) (1.14 g, 5.0 mmol) in THF (5 ml) was added at −70°. The resulting reaction mixture was stirred at −70° for 15 minutes and then at 0° for 1 hour.

The reaction mixture was diluted with EtOAc (100 ml) and water (100 ml) and the organic phase was separated, washed with brine and dried. Solvent removal gave a residue that was purified by flash chromatography on silcia gel eluting with hexane(9)/EtOAc(1) to give 1-9.

¹H NMR (300 MHz, CDCl₃) δ 0.30 (9H, s), 1.11 (2H, m), 1.45 (9H, s), 1.50–1.72 (3H, m), 2.03 (1H, t), 2.65 (2H, bt), 4.05 (2H, m), 5.50 (1d), 6.16 (1H, m).

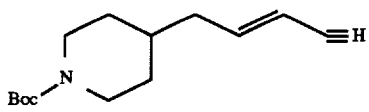

1-10

5-[4-(N-Boc-Piperidin-4-yl)]pent-3-ene-1-yne (1-10)

A solution of 1-9 (0.70 g, 2.18 mmol) in THF (60 ml) was diluted with H₂O (12 ml) and treated with LiOH·H₂O (0.96 g, 22.9 mmol) for 6 hours at room temperature. The reaction mixture was then diluted in H₂O (20 ml) and extracted with Et₂O. The organic extract was washed with brine, dried (MgSO₄) and the solvent removed. The residue was purified by flash chromatography on silica gel eluting with hexane (9)/EtOAc(1) to give 1-10.

¹H NMR (300 MHz, CDCl₃). δ 1.10 (2H, m), 1.45 (9H, s), 1.50–1.73 (3H, m), 2.07 (2H, m), 2.18 (2H, m), 4.09 (2H, m), 5.45 (1H, m), 6.20 (1H, m).

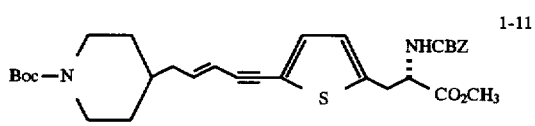

Methyl 5-{3-[5-[4-(N-Boc-Piperidin-4-yl)pent-3-ene-1-ynyl]}thien-2-yl-2-S-(N-benzyloxycarbonylamino)propanoate (1-11)

A solution of 1-6 (0.47 g, 1.28 mmol) and 1-10 (0.29 g, 1.16 mmol) in Et₂NH(6 ml) was treated with Pd(PPh₃)₂Cl₂ (0.045 g, 0.064 mmol) and cuprous iodide (0.006 g, 0.032 mmol) and the resulting mixture was stirred at room temperature for 16 hours.

The solvent was removed and the residue was taken up in Et₂O and washed with 10% citric acid solution, brine and dried (Na₂SO₄). Solvent removal gave a residue that was purified by flash chromatography on silica gel eluting with hexane(8)/EtOAc(2) followed by hexane(2)/EtOAc(1) to give 1-11 as an oil.

¹H NMR (300 MHz, CDCl₃) δ 1.12 (2H, m), 1.45 (9H, s), 1.55 (1H, m), 1.67 (3H, bd), 2.68 (2H, bt), 3.82 (2H, bs), 3.74 (3H, s) 4.08 (2H, m), 4.65 (1H, m), 5.12 (2H, s), 5.40 (1H, d), 5.68 (1H, m), 6.17 (1H, m), 6.60 (1H, m), 6.94 (1H, m), 7.35 (5H, m).

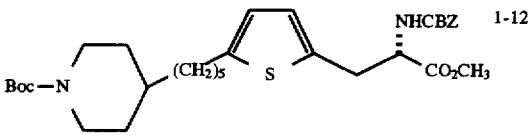

Methyl 3-{5-[5-[4-(N-Boc-piperidin-4-yl)pentyl]}thien-2-yl-2-S -(N-benzyloxycarbonylamino)propanoate(1-12)

A solution of 1-11 (0.040 g) in EtOH (10 ml) was treated with acetic acid (0.5 ml) and 10% Pd/C and this was hydrogenated (H₂) at atmospheric pressure for 1 hr. The catalyst was removed and the filtrate was concentrated to provide a residue. This was purified by flash chromatography on silica gel eluting with hexane(7)/EtOAc(3) to give 1-12 as an oil.

¹H NMR (300 MHz, CDCl₃) δ 1.07 (2H, m), 1.15–1.40 (7H, m), 1.45 (9H, s), 1.64 (4H, bd), 2.68 (4H, m), 3.27 (2H, m), 3.75 (3H, s), 4.05 (2H, m), 4.61 (1H, m), 5.38 (1H, m), 6.55 (2H, s), 7.32 (5H, m).

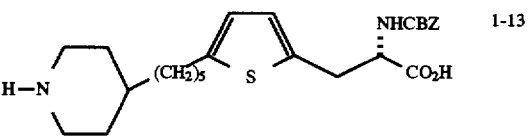

3-[5-{5-(4-Piperidinyl)pentyl}thien-2-yl]-2-(N-benzyloxycarbonylamino)propanoic acid (1-13)

A solution of 1-12 (0.093 g, 0.163 mmol) in THF(1)/ MeOH(1)/H₂O(1) (10 ml) was treated with LiOH·H₂O (0.068 g, 1.63 mmol) at room temperature for 3 hours. The solvent was then removed and the residue was acidified with 10% citric acid solution and extracted with EtOAc. The organic extract was washed with brine, dried (Na₂SO₄) and the solvent removed to provide the desired acid.

The acid was suspended in EtOAc (25 ml), cooled to −25° and treated with HCl gas for 0.5 hr. The resulting solution was then stirred at 0° for 2 hours. The solvent was removed and the residue was triturated with Et₂O to give 1-13, R$_f$ 0.35 [silica gel, EtOH(95)/NH₄OH(5)/H₂O(5)]

¹H NMR (300 MHz, CD₃OD) δ 1.30(8H, m), 1.52 (1H, m), 1.65 (2H, m), 1.84 (2H, bd), 2.72 (2H, t), 2.90 (2H, t), 3.16 (1H,m), 4.21 (1H, t), 5.09 (2H, m), 6.53 (1H, d), 6.59 (1H, d), 7.35 (5H, m).

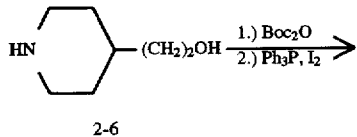

2-6

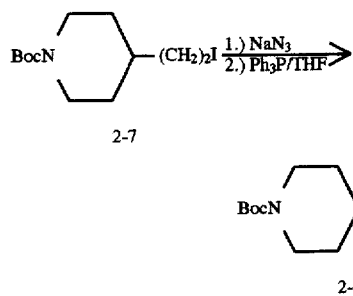

2-7

2-2

Preparation of 2-(N-Boc-4-Piperidinyl)ethylamine(2-2)
2-(N-Boc-4-Piperidinyl)ethyl iodide (2-7)

4-Piperidine-2-ethanol (Aldrich) (130 g, 1.0 mol) was dissolved in 700 mL dioxane, cooled to 0° C. and treated with 3N NaOH (336 mL, 1.0 mol), and di-t-butyldicarbonate (221.8 g, 1.0 mol). The ice bath was removed and the reaction stirred overnight. The reaction was concentrated, diluted with water and extracted with ether. The ether layers were combined, washed with brine, dried over MgSO₄, filtered and evaporated to give the desired BOC analog. R$_f$=0.37 in 1:1 EtOAc/Hexanes, ninhydrin stain.

¹H NMR (300MHz, CDCl₃) δ 4.07 (bs, 2H), 3.7 (bs, 2H), 2.7 (t,J=12.5 Hz, 2H), 1.8–1.6 (m, 6H), 1.51 (s, 9H), 1.1 (ddd, J=4.3, 12.5,12 Hz,2H).

This analog (10.42 g, 0.048 mol) was dissolved in 400 ml benzene and imidazole (4.66 g, 0.068 mol), iodine (0.05 mol and triphenylphosphine (15.24 g, 0.05 mol) were added at room temperature. After 6 hours the reaction mixture was filtered and the filtrate was evaporated to give a dark residue. This was purified by flash chromatography on silica gel eluting with 10% EtOAc-hexanes (R$_f$ 0.3) to give 2–7 as a yellow oil.

2-(N-Boc-4-Piperidinyl)ethylamine (2-2)

To 2-7 (27.9 g, 0.082 mol) dissolved in DMSO (400 ml) was added sodium azide (5.01 g, 0.086 mol) at room temperature and the resulting solution was heated at 65° for 2 hours. The cooled reaction mixture was diluted with 250 ml EtOAc, washed with brine and then dried (MgSO₄). Solvent removal provided the desired azide as a pale yellow oil, R$_f$ 0.5 (silica gel, 70% acetone/hexane).

To a solution of this azide (19.3 g, 0.076 mol) in THF (400 ml)/H₂O (195 ml) was added triphenylphosphine (80.0 g, 0.305 mol) in one portion at room temperature. This was stirred at room temperature 3 hours and the organic solvents were then removed in vacuo. The residue was acidified to pH 2 with 10% KHSO₄ solution and this was extracted 4×100 ml portions of EtOAc. The organic extract was extracted with 2×100 ml portions of 10% KHSO₄ and the aqueous phases were combined and the pH was adjusted to 10 with 2N NaOH. This solution was extracted with 4×200 ml portions of CH₂Cl₂. These were combined, dried (MgSO₄) and the solvent was removed to give 2-2 as an oil. R$_f$ 0.3 (silica gel, eluting with 10% CH₃OH in CHCl₃/ NH₃).

¹H NMR (300 MHz, CDCl₃) δ 4.05 (broad, 2H), 2.72 (t, J=7.2 Hz, 2H), 2.62 (m, 2H), 1.64 (d, J=12.2 Hz, 2H), 1.43 (s, 9H), 142–1.32 (m, 5H), 1.09 (m, 2H).

N-[2-(4-N-BOC-Piperdinyl)ethyl]-N'-[2-carboethoxyethyl]-2,5-thiophenedicarboxamide (2-4)

A solution of 2,5-thiophenedicarboxylic acid (Chemical Services) (0.17 g, 1.0 mmol) in DMF (10 ml) was treated at room temp with CDI (0.324 g, 2.0 mmol) followed by stirring for 1.0 hr. Then, 2-2 (0.23 g, 1.0 mmol) was added followed by stirring for 3 hours and then this was treated with βalanine ethyl ester HCl (0.15 g, 1.0 mmol) followed by Et₃N (0.11 g, 1.0 mmol). After stirring for 20 hours, the reaction mixture was poured into H₂O; acidified to pH 2–3 with 10% KHSO₄ solution and extracted with EtOAc. This was washed with brine, dried (MgSO₄), concentrated and the residue was purified by flash chromatography on silica gel eluting with 5% CH₃OH/CHCl₃ gave 2-4, R$_f$ 0.3.

N-[2-(4-Piperdinyl)ethyl]-N'-(2-carboxyethyl)-2,5-thiophenedicarboxamide (2-5)

A solution of 2-4 (0.58 g, 1.0 mmol) in 60 ml CH₃OH/ THF/H₂O (1:1:1) was treated at room temp with LiOH·H₂O (0.84 g, 20 mmol). After stirring for 4 hours the solvent was removed, the residue taken up in H₂O and extracted with EtOAc. The aqueous phase was acidified to pH 2–3 with 10% KHSO₄ solution and this was extracted with EtOAc. The combined organic phase extracts were dried (MgSO₄), concentrated, and the residue purified by flash chromatography on silica gel eluting with MeOH/HOAc/CHCl₃ (6:6:88) to give the desired acid.

¹H NMR (300 MHz, CD₃OD) δ 0.90 (2H, m), 1.11 (2H, m), 1.45 (9H, s), 1.55 (3H, m), 1.74 (2H, db), 2.51 (2H, m), 2.73 (1H, 6t), 3.70 (2H, m), 3.90 (2H, m), 3.61 (2H, m), 4.02 (2H, m), 7.60 (2H, s).

This acid (0.22 g, 0.47 mmoles) was dissolved in EtOAc(5 ml), cooled to –15°, treated with HCl gas for 15 minutes and then allowed to warm to 0°. After stirring for 1 hour, the solvent was removed and the residue purified by flash chromatography in silica gel eluting with 15% NH₄OH/EtOH to give pure 2-5.

¹H NMR (300 MHz, CD₃OD) δ 1.42 (2H, m), 1.61 (2H, m), 1.68 (1H, m), 2.12 (2H, bd), 2.62 (2H, t), 2.82 (2H, dt), 3.25 (1H, m), 3.40 (4H, m), 3.60 (2H, t), 7.62 (2H, s).

Preparation of Methyl 3-amino-2(S)-n-butylsulfonylamino-propionate hydrochloride (2-9) and Methyl 3-amino-2(S)-phenylsulfonylamino-propionate hydrochloride (2-9a)

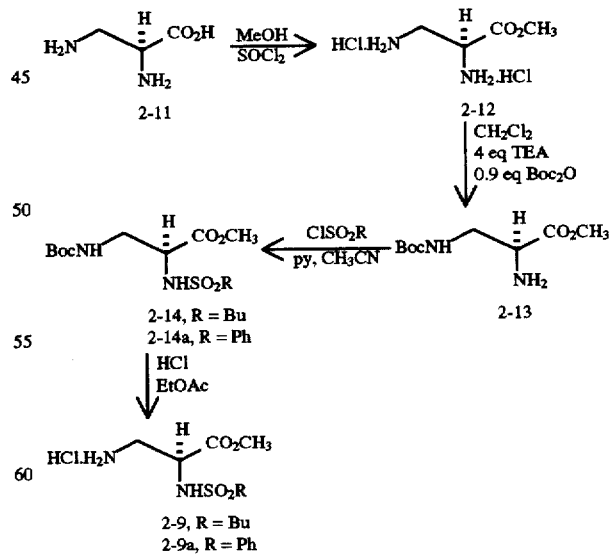

Methyl 2(S),3-Diaminopropionate dihydrochloride (2-12)

Methanol (400 mL) was cooled to 0° C. and thionyl chloride (217 mL, 3.0 mol, 20 eq) was added dropwise under argon. After addition was completed, the solution was warmed to RT for 20 minutes. 2(S), 3-Diaminopropionic acid (20 g, 0.143 mol) was crushed to a fine powder and added to the solution. The rxn was heated to reflux for 48 hrs, at which time TLC showed a small amount of starting material remaining. An additional portion of methanol (100 mL) and thionyl chloride (72 mL) was prepared as before and added to the reaction at RT; the reaction was then stirred overnight at RT. The reaction was worked up by removal of solvent at 40° C. in vacuo to provide 2-12. $R_f$ 0.72 (9:1:1 EtOH/H$_2$O/NH$_4$OH).

$^1$H NMR (400 MHz, D$_2$O) δ 4.55 (dd, J=5.4, 8.2 Hz, 1H), 3.92 (s, 3H), 3.64 (dd, J=8.2, 13.8 Hz, 1H), 3.55 (dd, J=5.4, 13.8 Hz, 1H).

Methyl [2(S)-Amino-3-(N-t-Butyloxycarbonylamino)]propionate (2-13)

2-12 (6.0 g, 31.5 mmol) was crushed to a fine powder, suspended in 1 L of CH$_2$Cl$_2$ and cooled to –78° C. under argon. Triethylamine (17.5 mL, 0.126 mol, 4 eq) was added dropwise as the solution gradually became homogeneous. Di-t-butyldicarbonate (6.18 g, 2.83 mmol, 0.9 eq) was dissolved in 50 mL CH$_2$Cl$_2$ and added dropwise to the solution. After the addition was completed, the reaction was placed in an ice bath and stirred for 1 ½ hours. The reaction was transferred to a separatory funnel and extracted with 3×50 mL of 10% KHSO$_4$ solution. The aqueous layer was washed with 3×10 mL of CH$_2$Cl$_2$, than basified with saturated NaHCO$_3$ and 3N NaOH solution to pH10 and extracted with 10×100 mL of CH$_2$Cl$_2$. The organic layer was dried with Na$_2$SO$_4$, filtered and evaporated to give 4.9 g of a pale yellow oil. Column chromatography in 2.5% MeOH/EtOAc gave 2-13 as an oil. $R_f$ 0.39 (5% MeOH/EtOAc).

$^1$H NMR (400 MHz, CDCl$_3$) δ 5.0 (bs, 1H), 3.72 (s, 3H), 3.56 (t, J=5.7 Hz, 1H), 3.46 (m, 1H), 3.23 (m, 1H), 1.55 (bs, 2H), 1.42 (s, 9H).

Methyl[2(S)-n-Butylsulfonylamino-3-N-t-butyloxycarbonylamino]-propionate (2-14)

2-13 was dissolved in acetonitrile (100 mL) and three portions of n-butylsulfonyl chloride (1.62 mL, 12.5 mmol, 1.1 eq each) and pyridine (1.0 mL, 12.5 mmol) were added over a period of three hours. The reaction was allowed to stir overnight, concentrated to ¼ its original volume, then diluted with 100 mL EtOAc and washed with 10% KHSO$_4$ (5×20 mL), dried with brine and MgSO$_4$, filtered and evaporated. Column chromatography in 20% –40% EtOAc/Hexane gave 2-14 as an oil. $R_f$ 0.6 (5% MeOH/CHCl$_3$).

$^1$H NMR (400 MHz, CDCl$_3$) δ 5.48 (bd, 1H), 4.9 (bs, 1H), 4.22 (m, 1H), 3.8 (s, 3H), 3.53 (m, 2H), 3.02 (m, 2H), 1.80 (m, 2H), 1.46 (m, 2H), 1.43 (s, 9H), 0.94 (t, J=7.4 Hz, 3H).

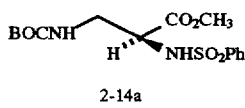

2-14a

Methyl 2(S)-(Phenylsulfonylamino)-3-(N-t-butylcarbonylamino)-propionate (2-14a)

Utilizing the procedure for converting 2-13 to 2-14, 2-13 (700 mg, 3.1 mmol) gave 2-14a (900 mg) as a white solid after flash chromatography (silica, 30% EtOAc/hexanes).

$^1$H NMR (400 MHz, CDCl$_3$) δ 7.85 (m, 2H), 7.60–7.50 (m, 3H), 5.67 (m, 1H), 4.00 (m, 1H), 3.56 (s, 3H), 3.47 (m, 2H), 1.45 (s, 9H).

Methyl 3-Amino-2(S)-n-butylsulfonylaminopropionate (2-9)

2-14 (2.0 g, 5.9 mmol) was dissolved in 30 mL of EtOAc and cooled to –40° C. HCl gas was bubbled through the solution until it was saturated, then the reaction was warmed to 0° C. and stirred for 1 hr. The excess HCl was removed under vacuum at room temperature and the reaction was concentrated at 35° C. to give 2-9 $R_f$ 0.6 (9:1EtOH/H$_2$O).

$^1$H NMR (400 MHz, CDCl$_3$) δ 8.8.1 (bs, 2H), 7.2 (m, 1H), 4.65 (m, 1H), 3.82 (s, 3H), 3.65 (m, 1H), 3.54 (m, 1H), 3.20 (bs, 2H), 1.8 (m, 2H), 1.45 (m, 2H), 0.95 (t, 1H, J=7.3 Hz).

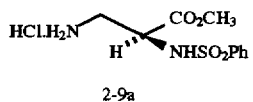

2-9a

Methyl 2(S)-(Phenylsulfonylamino)-3-aminopropionate-Hydrochloride (2-9a)

Utilizing the procedure for converting 2-14 to 2-9, 2-14a (900 mg) gave 2-9a (800 mg) as a white solid.

$^1$H NMR (400 MHz, CD$_3$OD) δ 7.88 (m, 2H), 7.65 (m, 1H), 7.60 (m, 1H), 4.25 (m, 1H), 3.42 (s, 3H), 3.35 (m, 1H), 3.10 (m, 1H).

N-[2-(4-N-Boc-Piperidinyl)ethyl]-N'-3-[methyl 2(S)-n-butylsulfonyl-aminopropionate]-2,5-thiophenedicarboxamide (2-10)

A solution of 2,5-thiophenedicarboxylic acid (2-1) (0.5 g, 2.9 mmol) in DMF (15 ml) was treated at room temp with CDI (5.8 mmol). After stirring for 10 minutes, 2-2 (0.66 g, 2.9 mmol) was added and this was stirred for 1 hr at room temp. Then, 2-9 (0.74 g, 2.9 mmol) was added followed by NMM (8.7 mmol) and the resulting mixture was stirred for 20 hrs. The reaction mixture was diluted with EtOAc, washed with H$_2$O, 10% KHSO$_4$, saturated NaHCO$_3$, brine, dried (MgSO$_4$) and concentrated. The residue was purified by flash chromatography on silica gel eluting with 75% EtOAc/hexanes ($R_f$ 0.2) to give pure 2-10.

$^1$H NMR (300 MHz, CDCl$_3$) δ 0.92 (3H, t), 1.14 (2H, m), 1.45 (9H, s), 1.57 (1H, m), 1.70 (2H, m), 1.80 (1H, m), 2.68 (2H, t), 3.05 (1H, t), 3.45 (2H, m), 3.70 (1H, m), 3.82 (3H, s), 3.90 (1H, m), 4.07 (2H, bd), 4.32 (1H, m), 5.68 (1H, d), 6.18 (1H, bt), 6.34 (1H, bt), 7.05 (1H, bt), 7.40 (1H, d), 7.45 (1H, s), 7.48 (1H, d).

N-2-(4-Piperidinyl)ethyl-N'-3-[2(S)-n-butylsulfonylaminopropionic acid]-2,5-thiophenedicarboxamide (2-15)

A solution of 2-10 (0.5 g, 86 mmol) in THF/CH$_3$OH/H$_2$O (9 ml) (1:1:1) at room temp was treated with LiOH (4.3 mmol) and after stirring for 3 hours the reaction was diluted with EtOAc and H$_2$O. The aqueous phase was washed with EtOAc and then acidified to pH 2-3 with 10% KHSO$_4$ solution and extracted with EtOAc. The organic phase was dried (MgSO$_4$) and concentrated to give the desired acid.

$^1$H NMR (300 MHz, CD$_3$OD) δ 0.90 (3H, t), 1.10 (1H, m), 1.45 (9H, s), 1.57 (2H, m), 1.76 (2H, m), 2.74 (2H, b), 3.03 (2H, t), 3.41 (2H, m), 3.58 (1H, dd), 3.80 (1H, dd), 4.05 (2H, bd), 4.29 (1H, dd), 7.62 (2H, m).

This acid (0.35 g, 0.59 mmol) was dissolved in EtOAc and treated with HCl gas as described for 2-9 to give 2-15. $R_f$ 0.28 (silica, EtOH/NH$_4$OH/H$_2$O(10:1:1).

$^1$H NMR (300 MHz, D$_2$O) δ 0.62 (3H, t), 1.29 (2H, m), 1.50 (4H, m), 1.85 (2H, bd), 2.81 (2H, dt), 2.97 (2H, t), 3.46 (1H, dd), 3.71 (1H, dd), 4.18 (1H, dd), 7.50 (2H, m).

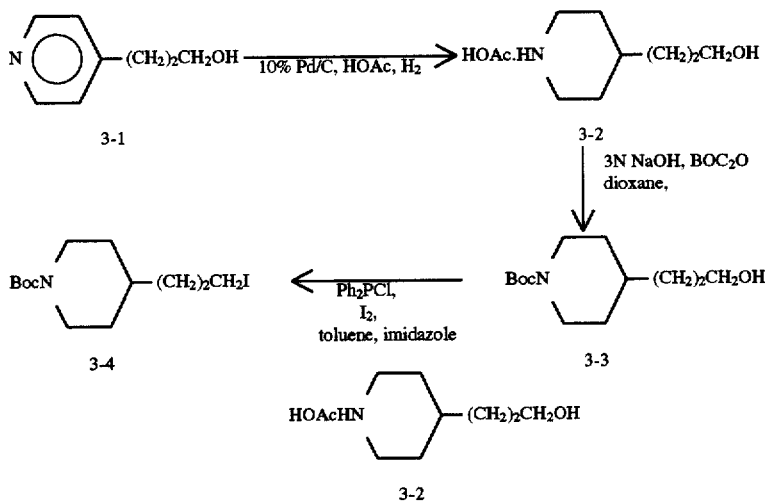

3-(Piperidin-4-yl)propanol acetic acid salt (3-2)

A mixture of 3-1 (15 g, 0.11 mol), HOAc (100 mL), and 10% Pd/C (2.0 g) was shaken on the Parr apparatus under a hydrogen atmosphere at 50 PSI for 2 days. The reaction mixture was then filtered through a celite pad and the filtrate concentrated to give 3-2 as a yellow oil.

$^1$H NMR (400 MHz, CDCl$_3$) δ 8.00 (bs, 2H), 3.62 (m, 2H), 3.17 (m, 2H), 2.78 (m, 2H), 2.01 (s, 3H), 1.82 (m, 2H), 1.60–1.30 (m, 7H).

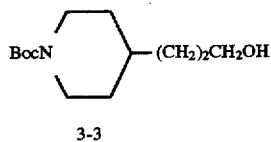

3-(N-Boc-Piperidin-4-yl)propanol (3-3)

A stirred solution of 3-2 (41.8 g, 0.14 mol), dioxane (300 mL), and 3N NaOH (0.51 mol, 170 mL) at ambient temperature was treated with di-butyl dicarbonate (32.1 g, 0.15 mol). After 24 h the dioxane was evaporated and the aqueous phase extracted with ether. The ethereal extracts were combined, washed with 10% KHSO$_4$ and brine, dried (MgSO$_4$), and then concentrated. Flash chromatography (silica, 30% to 50% EtOAc/ hexanes) gave 3-3 as an oil, R$_f$ 0.11 (silica, 20% EtOAc/hexanes).

$^1$H NMR (400 MHz, CDCl$_3$) δ 4.07 (m, 2H), 3.61 (t, J=7 Hz, 2H), 2.65 (m, 2H), 1.70–1.30 (m, 7H), 1.47 (s, 9H), 1.08 (m, 2H).

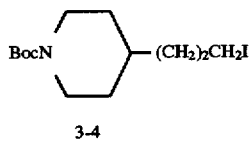

3-(N-Boc-Piperidin-4-yl)propyl iodide (3-4)

To a stirred mixture of 3-3 (22.7 g, 93 mmol), chlorodiphenylphosphine (21.7 mL, 0.12 mol), imidazole (19.0 g, 0.28 mol), and toluene (300 mL) at 0° C. was added iodine (30.6 g, 0.12 mol) in toluene (700 mL) followed by removal of the cooling bath. After 2.0 h the reaction mixture was washed with saturated Na$_2$CO$_3$, 5% Na$_2$S$_2$O$_3$, 10% KHSO$_4$ and brine, dried (MgSO$_4$), and concentrated. Flash chromatography (silica, 30% EtOAc/hexanes) gave 3-4 as a colorless oil, R$_f$ 0.41 (silica, 10% EtOAc/hexanes.

$^1$H NMR (400 MHz, CDCl$_3$) δ 4.05 (m, 2H), 3.20 (t, J=7 Hz, 2H), 2.65 (m, 2H), 1.80 (m, 2H), 1.62 (m, 2H), 1.48 (s, 9H), 1.38 (m, 3H), 1.10 (m, 2H).

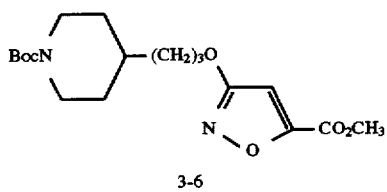

Methyl 3-[3-(N-BOC-Piperidin-4-yl)propyloxy]isoxazole-5-carboxylate (3-6)

A mixture of methyl 3-hydroxy-5-isoxazolecarboxylate (Aldrich) (3-5) (286 mg, 2.0 mmol), 3-4 (706 mg, 2.0 mmol), Cs$_2$CO$_3$ (650 mg, 2.0 mmol), and DMF (10 mL) was stirred at ambient temperature. After 72 hours the reaction mixture was diluted with ether and then washed with H$_2$O and brine, dried (MgSO$_4$), and concentrated. Flash chromatography (silica, 4% acetone/CH$_2$Cl$_2$) gave 3-6 as a colorless solid. R$_f$ 0.54 (silica, 40 %EtOAc/hexanes).

$^1$H NMR (300 MHz, CDCl$_3$) δ 6.52 (s, 1H), 4.27 (t, J=7 Hz, 2H), 4.09 (m, 2H), 3.95 (s, 3H), 2.68 (m, 2H), 1.82 (m, 2H), 1.67 (m, 2H), 1.40 (m, 3H), 1.46 (s, 9H), 1.11 (m, 2H).

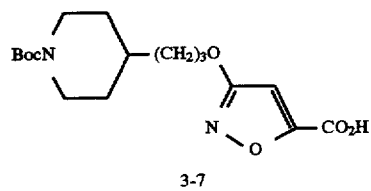

3-[3-(N-BOC-Piperidin-4-yl)propyloxy]isoxazole-5-carboxylic acid (3-7)

A solution of 3-6 (580 mg, 1.6 mmol), 1N NaOH (3.1 mL, 3.1 mmol), and CH$_3$OH (8 mL) was stirred at ambient temperature for 1.0 h. The reaction was then concentrated and the resulting gum acidified with 1M NaHSO$_4$. The aqueous layer was saturated with NaCl and then extracted with ether. The extracts were combined, dried (MgSO$_4$) and concentrated to give 3-7 as a viscous gum. R$_f$ 0.20 (silica, 9/0.5/0.5 CH$_2$Cl$_2$/CH$_3$OH/HOAc).

$^1$H NMR (300 MHz, CDCl$_3$) δ 8.35 (bs, 1H), 6.58 (s, 1H), 4.28 (t, J=7 Hz, 2H), 4.10 (m, 2H), 2.70 (m, 2H), 1.82 (m,

2H), 1.69 (m, 2H), 1.37 (m, 3H), 1.12 (m, 2H).

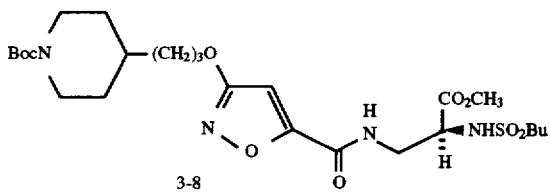

3-[3-(N-Boc-Piperidin-4-yl)propyloxy]isoxazole-5-carbonyl-2(S)-butylsulfonylamino-β-alanine methyl ester (3-8)

A stirred solution of 3-7 (142 mg, 0.4 mmol), 2-9 (110 mg, 0.4 mmol), HOBT (61 mg, 0.4 mmol), N(i-Pr)$_2$Et (216 μL, 1.2 mmol) and DMF (7 mL) at −15° C. was treated with EDC (77 mg, 0.4 mmol) followed by removal of the cooling bath. After 20 h, the reaction mixture concentrated followed by dilution with EtOAc. The EtOAc solution was washed with 1M NaHSO$_4$, and brine, dried (MgSO$_4$), and concentrated. Flash chromatography (silica, 10% to 20% acetone/CH$_2$Cl$_2$) to give 3-8 as a viscous gum. R$_f$0.64 (silica, 20% acetone/CH$_2$Cl$_2$).

$^1$H NMR (300 MHz, CDCl$_3$) δ 7.26 (t, J=4 Hz, 1H), 6.51 (s, 1H), 5.64 d, J=10 Hz, 1H), 4.36 (m, 1H), 4.24 (t, J=7 Hz, 2H), 4.10 (m, 2H), 3.82 (s, 3H), 3.82 (m, 2H), 3.04 (m, 2H), 2.68 (m, 2H), 1.80 (m, 4H), 1.67 (m, 2H), 1.45 (s, 9H), 1.40 (m, 2H), 1.10 (m, 2H), 0.92 (t, J=7 Hz, 3H).

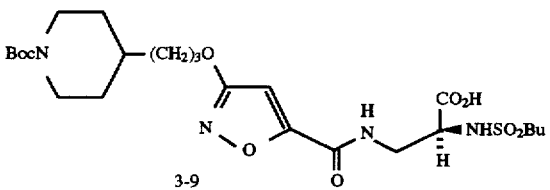

3-[3-(N-BOC-Piperidin-4-yl)propyloxy]isoxazole-5-carbonyl-2(S)-butylsulfonylamino-β-alanine (3-9)

A solution of 3-8 (1.86 mg, 0.32 mmol), LiOH.H$_2$O (67 mg, 1.6 mmol), H$_2$O (2 mL), and THF (8 mL) was stirred at ambient temperature for 1.0 h. The solution was acidified with 1M NaHSO$_4$ followed by evaporation of THF. The residue was partitioned between EtOAc and brine. The EtOAc layer was then dried (MgSO$_4$) and concentrated to give 3-9 as a pale yellow solid. R$_f$0.40 (silica, 9/.0.5/0.5 CH$_2$Cl$_2$:CH$_3$OH:HOAc).

$^1$H NMR (300 MHz, CDCl$_3$) δ 7.35 (m, 1H), 6.52 (s, 1H), 5.79 (d, J=8 Hz, 1H), 4.37 (m, 1H), 4.24 (t, J=7 Hz, 2H), 4.08 (m, 2H), 3.90 (m, 2H), 3.08 (m, 2H), 2.68 (m, 2H), 1.80 (m, 4H), 1.67 (m, 2H), 1.45 (s, 9H), 1.40 (m, 5H), 1.10 (m, 2H), 0.92 (t, J=7 Hz, 3H).

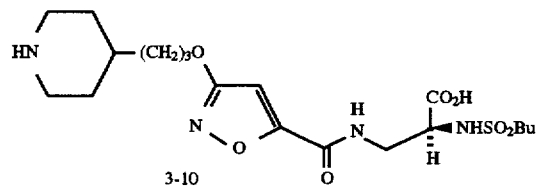

3-[3-(Piperidin-4-yl)propyloxy]isoxazole-5-carbonyl-2(S)-butyl-sulfonylamino-β-alanine (3-10)

A solution of 3-9 (180 mg, 0.32 mmol), TFA (2 mL), and CH$_2$Cl$_2$ (20 mL) was stirred at ambient temperature for 1.0 hour and then concentrated. Flash chromatography (silica, 9/1/1 ethanol/NH$_4$OH/H$_2$O) gave 3-10 as a pale yellow solid. R$_f$0.33 (silica, 9/1/1 ethanol/NH$_4$OH/H$_2$O).

$^1$H NMR (300 MHz, D$_2$O+NaOD) δ 6.66 (s, 1H), 4.27 (t, J=6 Hz, 2H), 3.76 (m, 1H), 3.61 (m, 1H), 3.36 (m, 1H), 2.92 (m, 2H), 2.82 (m, 2H), 2.48 (m, 2H), 1.82 (m, 2H), 1.62 (m, 4H), 1.35 (m, 5H), 1.05 (m, 2H), 0.82 (t, J=7 Hz, 3H).

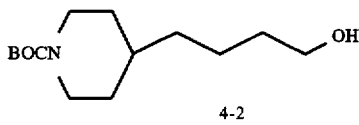

4-(N-BOC-Piperidin-4-yl)butanol (4-2)

A stirred solution of 4-1 (for preparation see EP0478362A2) (5.4 g, 20 mmol) in THF (20 mL) was treated with BH$_3$·THF (22 mL, 22 mmol) and stirred overnight. After 20 h more BH$_3$·THF (44 mL, 44 mmol) was added and the reaction mixture stirred for 4 h. The reaction was then quenched by careful addition of methanol (100 mL). After 30 min the solvents were evaporated, the residue dissolved in ether (200 mL) and the solution washed with sat.

NaHCO$_3$ and brine, dried (MgSO$_4$) and concentrated to give impure 4-2 as a colorless oil. R$_f$0.55 (silica, 10% acetone/CH$_2$Cl$_2$).

$^1$H NMR (300 MHz, CDCl$_3$) δ 4.05 (m, 2H), 3.62 (m, 2H), 2.64 (m, 2H), 1.70–0.9 (m, 1H), 1.45 (s, 9H).

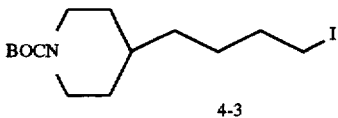

4-(N-BOC-Piperidin-4-yl)butyl iodide (4-3)

A mixture of 4-2 (3.4 g, 13.2 mmol), Ph$_3$P (5.2 g, 19.8 mmol), imidazole (2.7 g, 39.6 mmol), and THF (30 mL) at ambient temperature was treated with iodine (5.0 g, 19.8 mmol) in three portions. After 1 h most of the THF was evaporated and the residue partitioned between EtOAc and H$_2$O. The EtOAc layer was washed with H$_2$O, 10% Na$_2$S$_2$O$_3$, and brine, dried (MgSO$_4$) and concentrated to give a solid. Flash chromatography (silica, 10% EtOAc/hexanes) gave 4-3 (3.0 g) as a light yellow oil. R$_f$0.27 (silica, 10% EtOAc/hexanes).

$^1$H NMR (300 MHz, CDCl$_3$) δ 4.08 (m, 2H), 3.19 (t, J=7 Hz, 2H), 2.68 (m, 2H), 1.85–1.00 (m, 11H), 1.45 (s, 9H).

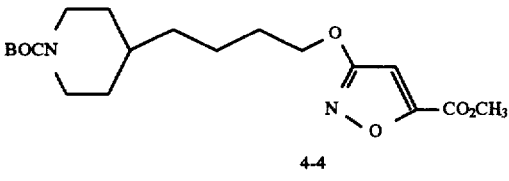

Methyl 3-[4-(N-BOC-Piperidin-4-yl)butyloxy]isoxazole-5-carboxylate (4-4)

A mixture of 4-3 (3.0 g, 8.1 mmol), Cs$_2$CO$_3$ (2.6 g, 8.1 mmol), methyl 3-hydroxy-5-isoxazolecarboxylate (Aldrich) (1.2 g, 8.1 mmol), and DMF (20 mL) was stirred at ambient temperature for 20 h. The reaction mixture was diluted with ether and then washed with H$_2$O and brine, dried (MgSO$_4$), and concentrated. Flash chromatography (silica, 3% acetone/CH$_2$Cl$_2$) gave 4-4 (2.7 g) as a colorless solid. R$_f$0.17 (silica, 3% acetone/CH$_2$Cl$_2$).

$^1$H NMR (300 MHz, CDCl$_3$) δ 6.53 (s, 1H), 4.28 (t, J=7 Hz, 2H), 4.08 (m, 2H), 3.95 (s, 3H), 2.65 (m, 2H), 1.85–1.00 (m, 11H), 1.45 (s, 9H).

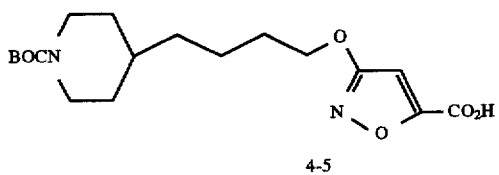

3-[4-(N-BOC-Piperidin-4-yl)butyloxy]isoxazole-5-carboxylic acid (4-5)

A solution of 4-4 (2.7 g, 6.9 mmol), $CH_3OH$ (50 mL), and 1N NaOH (13.9 mL, 13.9 mmol) was stirred at ambient temperature for 1 h. The $CH_3OH$ was evaporated and the resulting aqueous portion acidified with 1M $NaHSO_4$. The solution was extracted with EtOAc (3×) and then the extracts were combined, dried ($MgSO_4$), and concentrated to give 4-5 (2.5 g) as a solid.

$^1$H NMR (300 MHz, $CDCl_3$) δ 6.57 (s, 1H), 4.29 (t, J=7 Hz, 2H), 4.08 (m, 2H), 2.70 (m, 2H), 1.80–1.00 (m, 11H), 1.46 (s, 9H).

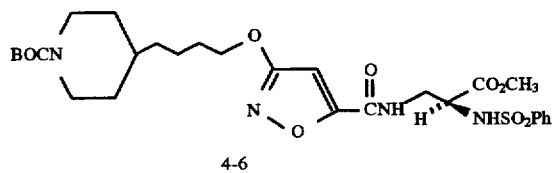

3-[4-(N-BOC-Piperidin-4-yl)butyloxy]isoxazole-5-carbonyl-2(S)-phenylsulfonylamino-β-alanine methyl ester (4-6)

A stirred mixture of 4-5 (147 mg, 0.4 mmol), 2-9a (149 mg, 0.4 mmol), HOBT (61 mg, 0.4 mmol), DIEA (215 μL, 1.2 mmol), and DMF (6 mL) at −15° C. was treated with EDC (77 mg, 0.4 mL) followed by removal of the cooling bath. After 72 h, the reaction mixture was diluted with EtOAc and then washed with 1M $NaHSO_4$ and brine, dried ($MgSO_4$), and concentrated. Flash chromatography (silica, 10% acetone/$CH_2Cl_2$) gave 4-6 (176 mg) as a viscous oil. $R_f$ 0.24 (silica, 10% acetone/$CH_2Cl_2$).

$^1$H NMR (300 MHz, $CDCl_3$) δ 7.87 (m, 2H), 7.50 (m, 3H), 7.09 (m, 1H), 6.48 (s, 1H), 5.83 (d, J=8 Hz, 1H), 4.26 (t, J=7 Hz, 2H), 4.09 (m, 2H), 3.78 (m, 2H), 3.61 (s, 3H), 2.67 (m, 2H), 1.85–1.00 (m, 11H), 1.45 (s, 9H).

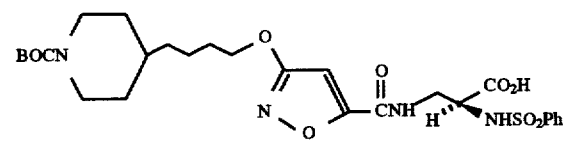

3-[4-(N-BOC-Piperidin-4-yl)butyloxy]isoxazole-5-carbonyl-2(S)-phenylsulfonylamino-β-alanine (4-7)

A solution of LiOH.$H_2O$ (35 mg, 0.87 mmol), 4-6 (176 mg, 0.29 mmol), and 20% aq. THF (10 mL) was stirred at ambient temperature for 1 h. The reaction mixture was acidified with 1M $NaHSO_4$ and extracted with EtOAc (3×). The combined extracts were dried ($MgSO_4$) and concentrated to give 4-7 (171 mg) as a foam. $R_f$ 0.73 (silica, 9:0.5:0.5 $CH_2Cl_2$/$CH_3OH$/AcOH).

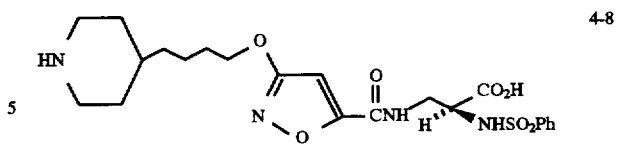

3-[4-(Piperidin-4-yl)butyloxy]isoxazole-5-carbonyl-2(S)-phenylsulfonylamino-β-alanine (4-8)

A solution of 4-7 (171 mg, 0.29 mmol), TFA (2 mL), and $CH_2Cl_2$ (20 mL) was stirred at ambient temperature for 1 h.

Concentration and flash chromatography (silica, 6:2:2 $CH_2Cl_2$/$CH_3OH$/AcOH) gave a semisolid which was triturated with ethanol/$NH_4OH$/$H_2O$ (9:1:1) and filtered to give 4-8 (86 mg) as a solid. $R_f$ 0.45 (silica, 6:2:2 $CH_2Cl_2$/$CH_3OH$/AcOH).

$^1$H NMR (300 MHz, $D_2O$) δ 7.68 (m, 2H), 7.28 (m, 3H), 6.42 (s, 1H), 4.31 (t, J=7 Hz, 2H), 3.70 (m, 1H), 3.58 (m, 1H), 3.17 (m, 1H), 2.93 (m, 2H), 1.80–1.00 (m, 11H).

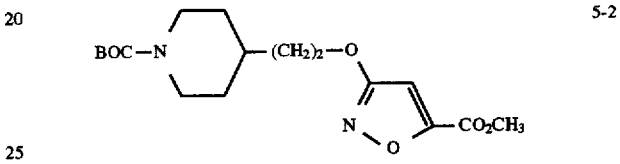

Methyl 3-[2-(N-BOC-Piperidin-4-yl)ethyloxy]isoxazole-5-carboxylate (5-2)

Utilizing the procedure for converting 4-3 to 4-4, 5-1 (0.68 g, 2.0 mmol) (European Publication 512,831) gave 5-2 (0.65 g) as viscous oil after flash chromatography (silica, 2%→5% acetone/$CH_2Cl_2$). $R_f$ 0.34 (silica, 2% acetone/$CH_2Cl_2$).

$^1$H NMR (300 MHz, $CDCl_3$) δ 6.53 (s, 1H), 4.36 (t, J=7 Hz, 2H), 4.08 (m, 2H), 3.95 (s, 3H), 2.69 (m, 2H), 1.80–1.10 (m, 7H), 1.46 (s, 9H).

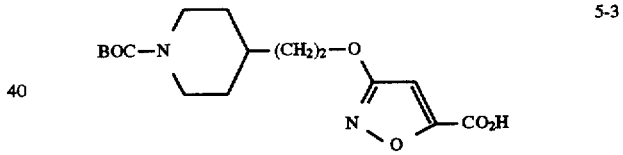

3-[2-(N-BOC-Piperidin-4-yl)ethyloxy]isoxazole-5-carboxylic acid (5-3)

Utilizing the procedure for converting 4-4 to 4-5, 5-2 (650 mg, 1.76 mmol) gave 5-3 (640 mg) as a colorless foam.

$^1$H NMR ($CDCl_3$) δ 6.58 (s, 1H), 4.35 (t, J=7 Hz, 2H), 4.10 (m, 2H), 2.71 (m, 2H), 1.80–1.10 (m, 7H), 1.46 (s, 9H).

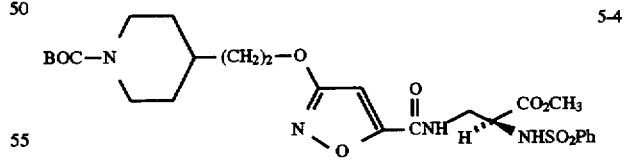

3-[2-(N-BOC-Piperidin-4-yl)ethyloxy]isoxazole-5-carbonyl-2(S)-phenylsulfonylamino-β-alanine methyl ester (5-4)

Utilizing the procedure for converting 4-5 to 4-6, 5-3 (136 mg, 0.4 mmol) gave 5-4 (172 mg) as a viscous oil after flash chromatography (silica, 15% acetone/$CH_2Cl_2$). $R_f$ 0.31 same system.

$^1$H NMR (300 MHz, $CDCl_3$) δ 7.86 (m, 2H), 7.52 (m, 3H), 7.20 (m, 1H), 5.97 (d, J=8 Hz, 1H), 4.32 (t, J=7 Hz, 2H), 4.15 (m, 1H), 4.08 (m, 2H), 3.78 (m, 2H), 3.60 (s, 3H), 2.70 (m, 2H), 1.80–1.10 (m, 7H), 1.46 (s, 9H).

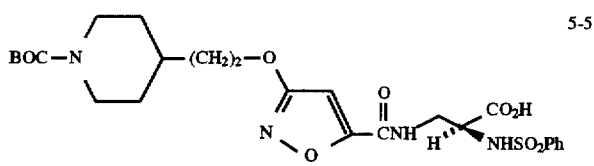

3-[2-(N-BOC-Piperidin-4-yl)ethyloxy]isoxazole-5-carbonyl-2-(S)-phenylsulfonyl-amino-β-alanine (5-5)

Utilizing the procedure for converting 4-6 to 4-7, 5-4 (172 mg, 0.29 mmol) gave 5-5 (160 mg) as a viscous oil. $R_f$ 0.48 (silica, 9:0.5:0.5 $CH_2Cl_2/CH_3OH$, AcOH).

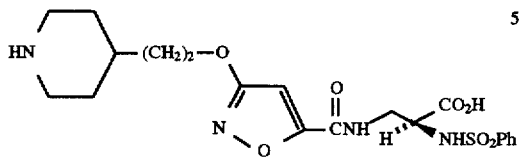

3-[2-(Piperidin-4-yl)ethyloxy]isoxazole-5-carbonyl-2(S)-phenylsulfonylamino-β-alanine (5-6)

Utilizing the procedure for converting 4-7 to 4-8, 5-5 (160 mg, 0.28 mmol) gave 5-6 (114 mg) after flash chromatography (silica, 9/1/1 ethanol/$NH_4OH/H_2O$). $R_f$ 0.32 (silica, 9/1/1 ethanol/$NH_4OH/H_2O$).

$^1$H NMR (300 MHz, $D_2O$ & NaOD) δ 7.68 (m, 2H), 7.29 (m, 3H), 6.43 (s, 1H), 3.69 (m, 1H), 3.57 (m, 1H), 3.16 (m, 1H), 2.95 (m, 2H), 2.52 (m, 2H), 1.75 (m, 5H), 1.16 (m, 2H). Sample alternative protecting groups that can be used in the preparation of the present invention include benzyl ester, cyclohexyl ester, 4-nitrobenzyl ester, t-butyl ester, 4-pyridylmethyl ester, benzyloxycarbonyl, isonicotinyloxycarbonyl, p-methoxybenzyloxycarbonyl, t-butoxycarbonyl, t-amyloxycarbonyl, isobornyloxycarbonyl, adamantyloxycarbonyl, 2-(4-biphenyl)-2-propyloxycarbonyl and 9-fluorenylmethoxycarbonyl.

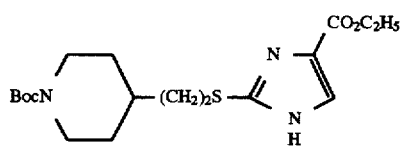

2-[2-(N-BOC-Piperidin-4-yl)ethylthio]imidazole-4-carboxylic acid ethyl ester (6-2)

Imidazolethiol 6-1 (108 mg, 0.63 mmol) was dissolved in 1 mL DMF at 0° C., NaHMDS (1M, 0.63 mL, 0.63 mmol) was added, and after 5 min, iodide 5-1 (190 mg, 0.60 mmol) dissolved in 1 mL THF was added. After 1 h the mixture was diluted with EtOAc, washed with sat. $NaHCO_3$, water, and brine, dried ($MgSO_4$), and concentrated. Flash chromatography (silica, 40% EtOAc/hexane) provided crystalline 6-2. $R_f$ 0.19 (40% EtOAc/Hexane); $^1$H NMR (400 MHz, $CDCl_3$) δ 9.55 (br s, 1H), 7.66 (s, 1H), 4.34 (m, 2H), 4.09 (br m, 2H), 3.20 (t, J=7 Hz, 2H), 2.67 (m, 2H), 1.70–1.52 (m, 5H), 1.45 (s, 9H), 1.37 (t, J=7 Hz, 3H), 1.11 (m, 2H).

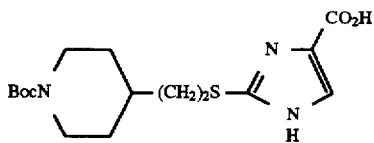

2-[2-(N-BOC-Piperidin-4-yl)ethylthio]imidazole-4-carboxylic acid (6-3)

6-2 (162.5 mg, 0.42 mmol) was dissolved in 3 mL MeOH NaOH (1N, 0.5 mL, 0.5 mmol) was added; after 6 h additional NaOH (1N, 1 mL, 1 mmol) was added; after 1 day additional NaOH (1N, 1 mL, 1 mmol) was added. After three more days the mixture was heated at 50° for 6 h, then concentrated. The residue was taken up in water, pH adjusted to 5 with 5% $KHSO_4$, extracted 3× with EtOAc, the combined organic extracts were washed with brine, dried ($MgSO_4$), and concentrated providing acid 6-3. $R_f$ 0.39 (9:1:1 $CH_2Cl_2$/MeOH/HOAc);

$^1$H NMR (400 MHz, $CDCl_3$) δ 7.75 (s, 1H), 4.08 (m, 2H), 3.20 (t, J=7 Hz, 2H), 2.70 (m, 2H), 1.70–1.52 (m, 5H), 1.45 (s, 9H), 1.12 (m, 2H).

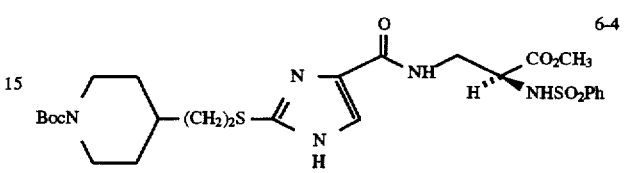

2-[2-(N-BOC-Piperidin-4-yl)ethylthio]imidazole-4-carbonyl-2(S-phenylsulfonylamino-β-alanine methyl ester (6-4)

6-3 (70 mg, 0.20 mmol) and amine hydrochloride 2-9a (72 mg, 0.24 mmol), were combined with EDC (48 mg, 0.25 mmol), HOBT (40 mg, 0.30 mmol), and NMM (121 μL, 1.1 mmol) in 2 mL DMF at 0° C. After warming to RT for 4 days, the mixture was concentrated and purified by flash chromatography (silica, EtOAc), providing 6-4. $R_f$ 0.54 (EtOAc); $^1$H NMR (400 MHz, $CDCl_3$) δ 7.85 (dd, J=9.1 Hz, 2H), 7.61 (d, J=2 Hz, 1H), 7.56–7.43 (m, 3H), 6.33 (br s, 1H), 4.18–4.00 (m, 3H), 3.83–3.62 (m, 3H), 3.57 (s, 3H), 3.09 (t, J=7 Hz, 2H), 2.68 (br m, 2H), 1.70–1.53 (m, 5H), 1.45 (s, 9H), 1.09 (m, 2H).

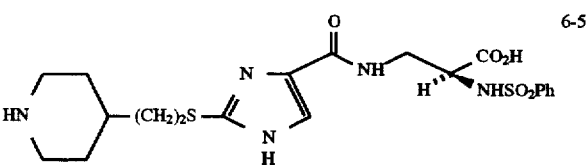

2-[2-Piperidin-4-yl)ethylthio]imidazol-4-carbonyl-2(S)-phenylsulfonylamino-β-alanine (6-5)

A mixture of 6-4 (68.2 mg, 0.108 mmol) in 5 mL 6N HCl was heated at 60° C. for 2 h. Concentration and flash chromatography (silica, 10:1:1 EtOH/$NH_4OH/H_2O$) provided 6-5. $R_f$ 0.26 (10:1:1 EtOH/$H_2O$/conc. $NH_4OH$); $^1$H NMR (400 MHz, $D_2O$)δ7.77 (d, J=6 Hz, 2H), 7.57 (s, 1H), 7.47–7.37 (m, 3H), 3.93 (dd, J=10, 4 Hz, 1H), 3.70 (dd, J=14, 4 Hz, 1H), 3.41—3.35 (m, 3H), 3.09 (t, J=7 Hz, 2H), 2.95 (td, J=13, 3 Hz, 2H), 1.9 (br d, 2H), 1.75 (m, 1H), 1.64 (q, J=7 Hz, 2H), 1.37 (m, 2H); MS m/e calc'd for $C_{14}H_{23}N_4O_3S$: 327.1491, found 327.1509.

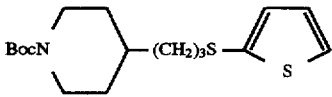

2-[3-(N-BOC-Piperidin-4-yl)prop-1-ylthio]thiophene (7-2)

2-Lithiothiophene (7-1) (1M in THF, 5.66 mL, 5.66 mmol) was diluted in 56 mL, THF at −78° C., then treated with sulfur (199 mg, 6.23 mmol). Once the sulfur was completely dissolved (ca. 1 h), a solution of iodide 3-4 (2.0 g, 5.66 mmol) in THF was added. The reaction was allowed to warm to RT over night, then diluted with EtOAc, washed with water and brine, dried ($MgSO_4$), and concentrated. Flash chromatography (silica, 5% EtOAc/hexane) provided 7-2 as a red oil.: $R_f$ 0.49 (10% EtOAc/Hexane); $^1$H NMR (300 MHz, CDCl₃)δ7.33 (dd, J=5, 1 Hz, 1H), 7.10 (dd, J=4, 1 Hz, 1H), 6.97 (dd, J=5, 4 Hz, 1H), 4.05 (br d, 2H), 2.77 (t, J=7 Hz, 2H), 2.65 (br t, 2H), 1.68–1.55 (m, 4H), 1.45 (s, 9H), 1.40–1.30 (m, 3H), 1.07 (m, 2H).

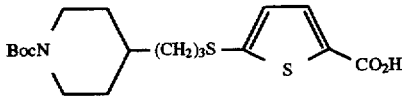

2-[3-(N-BOC-Piperidin-4-yl)prop-1-ylthio]thiophene-5-carboxylic acid (7-3)

A solution of thiophene 7-2 (1.28 g, 3.75 mmol) in THF (75 mL) was cooled to –78° and treated with n-BuLi (1.6M, 4.9 mL, 7.9 mmol). After 30 min, CO₂ (g) was bubbled into the mixture for 15 min, and the reaction was warmed to RT over night. After diluting with EtOAc, the acidic components were extracted into 1N NaOH. The aqueous base was acidified with 10% KHSO₄, extracted with EtOAc, and this organic layer was washed with brine, dried (MgSO₄), and concentrated to a yellow oil, which was used without purification.: R$_f$ 0.53 (45:1:1 CH₂Cl₂/MeOH/HOAc); ¹H NMR (400 MHz, DMSO-d₆)δ7.60 (d), 7.13(d), 3.90(m), 2.94(m), 2.62(m) 2.17(t), 1.57(br d), 1.50–1.25(m), 1.36(s), 0.92 (m).

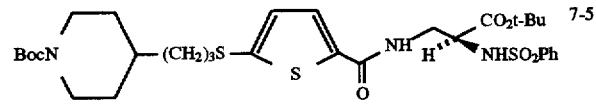

2-[3-(N-BOC-Piperidin-4-yl)prop-1-ylthio]thiophene-5-carbonyl-2(S)-phenylsulfonylamino-β-alanine-t-butyl (7-5)

Acid 7-3 (500 mg, 1.30 mmol), amine hydrochloride 7-4 (390 mg, 1.30 mmol), HOBT (210 mg, 1.7 mmol), EDC (299 mg, 1.7 mmol), and NMM (428 μL, 3.9 mmol) were combined in 10 mL DMF at –15° C., then allowed to warm to room temperature over night. The mixture was diluted with EtOAc, washed with water, 10% KHSO₄, sat.

NaHCO₃, and brine, dried (MgSO₄), and concentrated. Flash chromatography (silica, 30% EtOAc/hexane) provided 7-5.: R$_f$0.27 (40% EtOAc/Hexane); ¹H NMR (400 MHz, CDCl₃)δ7.8 (d, J=8 Hz, 2H), 7.60–7.46 (m, 3H), 7.40 (d, J=4 Hz, 1H), 6.97 (d, J=4 Hz, 1H), 6.80 (t, J=6 Hz, 1H), 6.57 (t, J=5 Hz, 1H), 5.65 (d, J=8 Hz, 1H), 4.08 (m, 2H), 3.90–3.85 (m, 2H), 3.53 (m, 1H), 2.88 (t, J=7 Hz, 2H), 2.66 (br t, 2H), 1.70–1.60 (m, 4H), 1.45 (s, 9H), 1.36 (m, 2H), 1.29 (s, 9H), 1.08 (m, 2H).

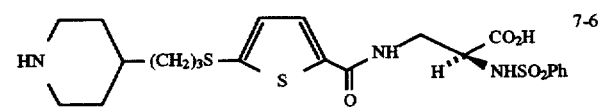

2-[3-(Piperidin-4-yl)prop-1-ylthio]thiophene-5-carbonyl-2(S)-phenylsulfonylamino-β-alanine (7-6)

A solution of 7-5 (78 mg, 0.116 mmol) and anisole (25 μL, 0.23 mmol) in 1.2 mL CH₂Cl₂/TFA (1:1) was stirred at 0° for 3 h, then concentrated. Flash chromatography (silica, 10:1:1 EtOH/H₂O/conc. NH₄OH), then preparative HPLC (C-18) provided 7-6.: ¹H NMR (400 MHz, D₂O)δ7.57 (d, 2H), 7.20–7.13 (m, 3H), 7.07 (d, 1H), 6.90 (d, 1H), 4.03 (dd, 1H), 3.54 (dd, 1H), 3.25–3.13 (m, 3H), 2.80–2.68 (m, 4H), 1.70 (d, 2H), 1.50 (qn, 2H), 1.40 (m, 1H), 1.22 (m, 2H), 1.15 (m, 2H); MS m/e calc'd for C₂₂H₃₀N₃O₅S₃: 512.134761, found 512.133575.

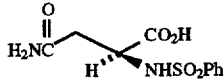

N-Phenylsulfonyl-L-Asparagine (7-8)

To a stirred solution of L-asparagine (Aldrich) (10 g, 76 mmol), NaOH (3.4 g, 85 mmol), H₂O(50 mL), and dioxane (50 mL) at 0°C. was added PhSO₂Cl(10.6 mL, 84 mmol). After 1 min. NaOH (3.4 g) in H₂O(50 mL) was added and the reaction mixture stirred for 30 min. The reaction mixture was then concentrated to remove the dioxane, then washed with EtOAc. The aqueous phase was then cooled to 0° C. and acidified to pH 2–3 with conc. HCl to effect product precipitation. The resulting solid was collected by filtration, washed with H₂O(20 mL) and dried at 50° C. under vacuum to give 7-8 as a white solid. R$_f$0.40 (silica, 10:1:1 ethanol/H₂O/NH₄OH). ¹H NMR (300 MHz, D₂O)δ7.59 (m, 2H), 7.26 (m, 3H), 3.92 (m, 1H), 3.02 (m, 1H), 2.35 (m, 1H).

2(S)-Phenylsulfonylamino-3-aminopropionic acid (7-9)

To a stirred solution of NaOH (15.6 g, 0.4 mol), in H₂O (70 mL), cooled with an ice bath, was added bromine (3.6 mL, 0.07 mol) dropwise. After 5 min, a cold solution of 7-8 (14.6 g, 54 mmol) and NaOH (4.3 g, 0.1 mol) in H₂O(50 mL) was added in one portion.

The solution was stirred for 20 min. at 0° C. then 30 min at 90° C. The reaction mixture was recooled to 0° C. and the pH adjusted to 7 through dropwise addition of conc. HCl. The white precipitate formed was collected by filtration and dried to give 7-9 as a white solid. ¹H NMR 300 MHz, D₂O)δ8.00–7.50 (m, 5H), 3.88 (m, 1H), 3.37 (m, 1H), 3.12 (m, 1H).

t-Butyl 2(S)-Phenylsulfonylamino-3-aminopropionate hydrochloride (7-4)

In a Fischer-Porter tube, a mixture of 7-9 (10.2 g, 42 mmol) and DME (150 mL) was sequentially, treated with H₂SO₄ (6.4 mL, 0.12 mol), cooled to –78° C., and then condensed isobutylene (75 mL). The cooling both removed. After 2h, ice/water (250 mL) was added followed by washing with ether (2×). The aqueous phase was basified with aq 6N NaOH, then saturated with NaCl followed by extraction with EtOH (3×). The combined extracts were washed with brine, dried (MgSO₄), and concentrated to give a white solid. This was dissolved in CHCl₃ then treated with 1N HCl/ether (22 mL) then concentrated to give 7-4 as a glossy yellow solid.

¹H NMR (400 MHz, DMSO)δ8.25–8.00 (m, 4H), 7.85–7.58 (m, 5H), 4.08 (m, 1H), 3.10 (m, 1H), 2.73 (m, 1H), 1.17 (s, 9H).

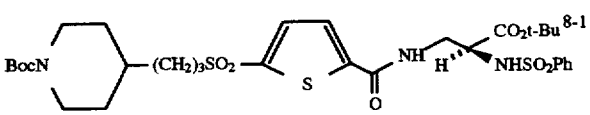

2-[3(N-BOC-Piperidin-4-yl)prop-1-ylsulfonyl]thiophene-5-carbonyl-2(S)-phenylsulfonylamino-β-alanine t-butyl (8-1)

Oxone (424 mg, 0.69 mmol) was added to a solution of 7-5 (157 mg, 0.23 mmol) in 2.3 mL MeOH. After 2 h the white suspension was concentrated, diluted with EtOAc, washed with water, then brine, dried (MgSO₄), and concentrated. Flash chromatography (silica, 50% EtOAc/Hexane) provided 8-1.: R$_f$0.37 (60% EtOAc/Hexane); ¹H NMR (400 MHz, CDCl₃)δ7.85 (dd, J=8, 0.5 Hz, 2H), 7.62–7.51 (m, 5H), 7.07 (t, J=6 Hz, 1H), 5.82 (d, J=8 Hz, 1H), 4.1 (m, 2H), 3.96–3.88 (m, 2H), 3.54 (m, 1H), 3.20 (m, 2H), 2.65 (m, 2H), 1.80 (m, 2H), 1.70 (br s, 1H), 1.61 (d, J=12 Hz, 2H), 1.45 (s, 9H), 1.40–1.25 (m, 2H), 1.30 (s, 9H), 1.08 (m, 2H).

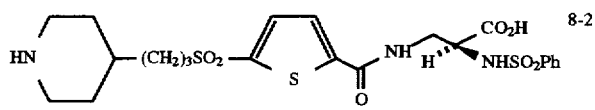

2-[3-(Piperidin-4-yl)prop-1-ylsulfonyl]thiophene-5-carbonyl-2(S)-phenylsulfonylamino-β-alanine (8-2)

A solution of 8-1 (62 mg, 0.088 mmol) and Et₃SiH (35 μL, 0.22 mmol) in 1 mL CH₂Cl₂/TFA (1:1) was stirred for 4.5 hr. Concentration of the reaction mixture, and flash chromatography (silica 10:1:1 EtOH/H₂O/conc. NH₄OH) provided 8-2.: R$_f$0.22 (10:1:1 EtOH/H₂O/conc. NH₄OH); ¹H NMR (400 MH, D₂O) δ 7.60–7.55 (m, 3H), 7.26 (m, 1H), 7.22–7.17 (m, 3H), 4.11 (dm, 1H), 3.61 (dm, 1H), 3.35 (m, 2H), 3.29 (m, 1H), 3.18 (d, 2H), 2.72 (t, 2H), 1.70 (d, 2H), 1.60 (m, 2H), 1.40 (m, 1H), 1.22 (m, 2H), 1.16 (m, 2H); MS (Positive FAB) m/e calc'd for C₂₂H₃₀N₃O₇S₃ 544.12459, found 544.12465; 544 (M+1);

SCHEME 9

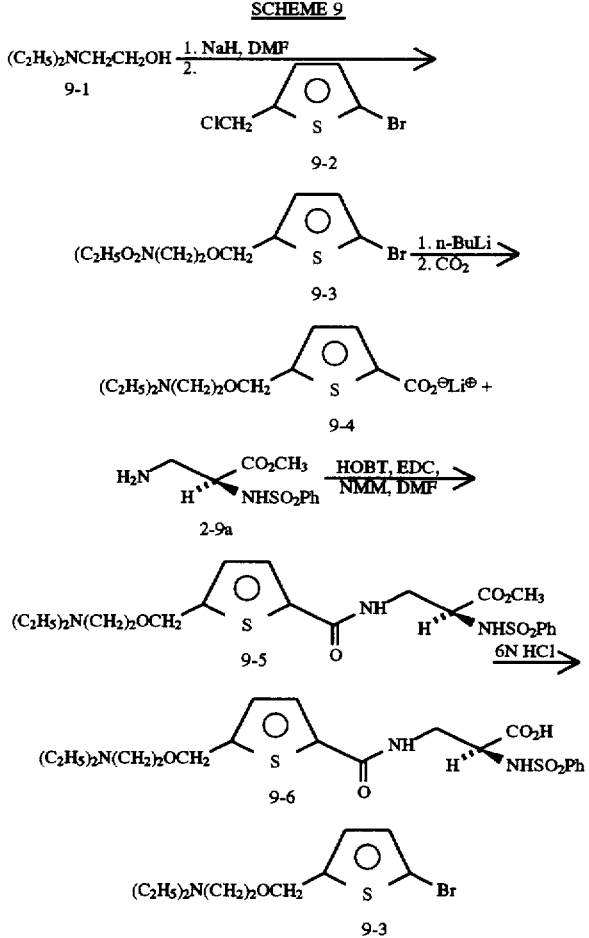

5-[2-N,N-Diethylaminoethyl)oxymethyl]-2-bromothiophene (9-3)

A solution of 9-1 (1.17 g, 10 mmol) (Aldrich) in DMF (10 ml) was treated with NaH (0.26 g, 11 mmol) for 15 min at room temperature and after cooling to 0°–10°, 9-2 (2.12 g, 10 mmol) (R. C. Clapp, et. al., *J. Am. Chem. Soc.* 1947, 69 1549) in 5 ml DMF was added. This was stirred for 2 hours and then extracted with 1N KHSO₄ solution and ether. The residue extract was made basic with Na₂CO₃ solution and extracted with EtOAc. The organic extract was dried (MgSO₄), concentrated and residue was purified by flash chromatography on silica gel eluting with chloroform/saturated NH₃ to give pure 9-3 as an oil.

¹H NMR (300 MHz, CDCl₃) δ 1.02 (6H, t, J=7.14), 2.56 (4H, q, J=7.14), 2.66 (2H, t), 2.88 (1H, s), 2.96 (1H, s), 3.54 (2H, t), 4.60 (2H, s), 6.73 (1H, d), 6.90 (1H, d).

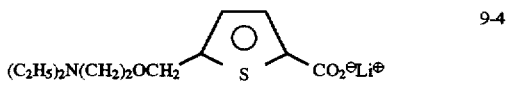

5-[(2-N,N-Diethylaminoethyl)oxymethyl]-2-thiophene carboxylic acid lithium salt (9-4)

A solution of 9-3 (0.29 g, 1 mmol) in THF was cooled to −78° and treated with n-BuLi (1 mmol). After stirring for 10 minutes this solution was poured into solid powdered CO₂ covered with ether and this was allowed to warm to room temperature with stirring. The solvent was removed to give 9-4 as a gummy solid.

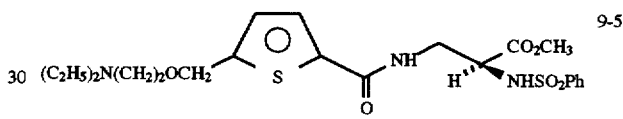

5-[(2-N,N-Diethylaminoethyl)oxymethyl]thiophene-2-carbonyl-2(S)-phenylsulfonylamino-β-alanine methyl ester (9-5)

A solution of 9-4 (1 mmol), 2-9a (0.3 g, 1 mmol), and HOBT (0.15 g, 1.1 mmol) in DMF (10 ml) at room temperature was treated with N-methylmorpholine (0.3 g, 3.0 mmol) followed by EDC (0.22 g, 1.16 mmol) and the resulting solution was stirred for 16 hours. The reaction mixture was diluted with EtOAc (100 ml) and saturated Na₂CO₃ solution,. The organic phase was washed with H₂O, dried (MgSO₄), concentrated and the residue was purified by flash chromatography on silica gel eluting with 7% CH₃OH/CHCl₃ saturated with NH₃ to pure 9-5.

¹H NMR (300 MHz, CDCl₃) δ 1.03 (6H, t), 2.57 (4H, q), 2.66 (2H, t), 3.58 (2H, m), 3.62 (3H, s), 3.70 (1H, m), 3.82 (1H, m), 4.05 (1H, m), 4.66 (2H, s), 6.92 (2H, m), 7.39–7.53 (4H, m), 7.83 (2H, m).

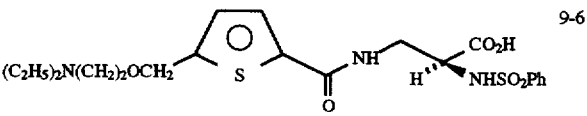

5-[(2-N,N-Diethylaminoethyl)oxymethyl]thiophene-2-carbonyl-2(S)-phenylsulfonylamino-β-alanine (9-6)

A solution of 9-5 (0.1 g, 0.21 mmol) in 6N HCl (5 ml) was stirred at room temperature for 16 hours. The solvent was then removed at low pressure to give 9-6.

SCHEME 10

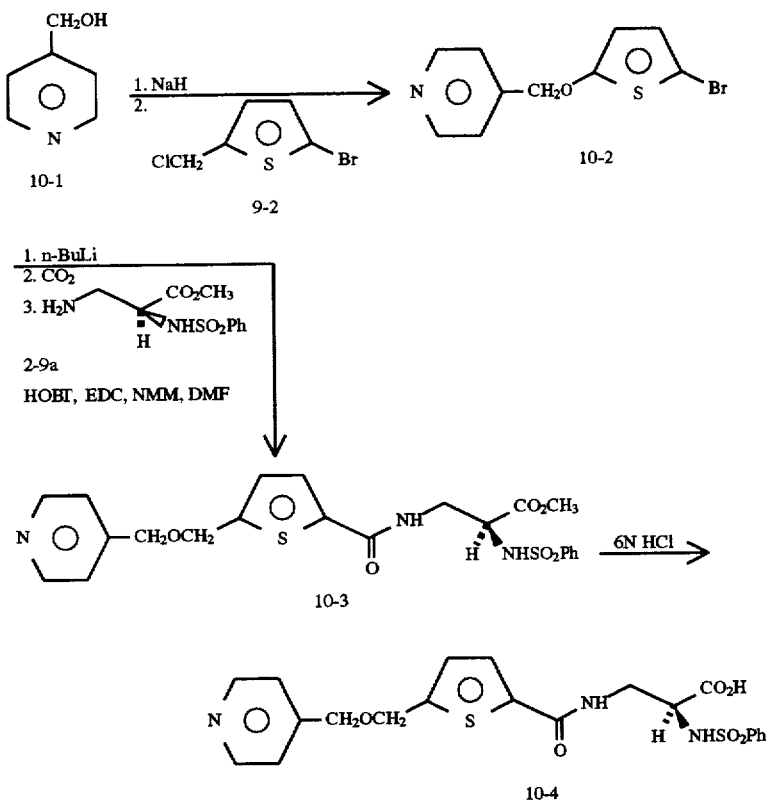

5-(4-Pyridylmethyloxymethyl)-2-bromothiophene (10-2)

A solution of 4-pyridinolmethanol (10-1) (1.04 g, 10 mmol) (Aldrich) in DMF (10 ml) at room temp. was treated with NaH (0.26 g, 11 mmol) and after stirring for 15 minutes, 9-2 (2.12 g, 10 mmol) in DMF (2 ml) was added at 0°–10°. After stirring at room temp. for 3 hours this mixture was diluted with EtOAc (100 ml) and $H_2O$ (100 ml). The organic phase was dried ($MgSO_4$), concentrated, and the residue was purified by flash chromatography on silica gel eluting with 2% $CH_3OH/CHCl_3$ to give pure 10-2.

$^1$H NMR (300 MHz, $CDCl_3$) δ 4.55 (2H, s), 4.67 (2H, s), 6.77 (1H, d), 6.94 (1H, d), 7.27 (2H, m), 8.58 (2H, dd).

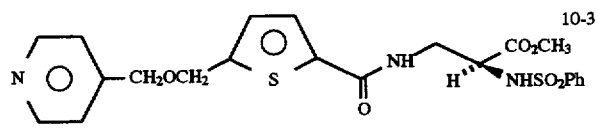

5-(4-Pyridylmethyloxymethyl)thiophene-2-carbonyl-2(S)-phenylsulfonylamino-β-alanine methyl ester (10-3)

A solution of 10-2 (0.28 g, 1 mmol) in THF cooled to –78° was treated with n-BuLi (1 mmol) and after stirring for 5 minutes this was poured onto solid $CO_2$ covered with $Et_2O$. This was stirred at ambient temperature as the mixture warmed to room temp. The solvent was then removed to give the desired carboxylic acid salt, as a tacky solid.

This salt (1 mmol) was dissolved in DMF (15 ml) along with 2-9a (0.3 g, 1 mmol) and HOBT (0.15 g, 1.1 mmol) and this solution was treated with N-methylmorpholine (0.3 g, 3.0 mmol) followed by EDC (0.22 g, 1.16 mmol). After stirring for 16 hours the reaction mixture was diluted with EtOAc (100 ml) and saturated $NaHCO_3$ solution (25 ml). The organic phase was washed with $H_2O$, dried ($MgSO_4$), concentrated and the residue was purified by flash chromatography on silica gel eluting with 1% $CH_3OH/EtOAc$ to give 10-3.

$^1$H NMR (300 MHz, $CDCl_3$) δ3.58 (3H, s), 3.70 (1H, m), 3.80 (1H, m), 4.12 (1H, m), 4.58 (2H, s), 4.72 (2H, s), 6.56 (1H, m), 6.93 (1H, d), 7.02 (1H, m), 7.27 (1H, d), 7.4–7.65 (4H, m), 7.83 (2H, m), 8.58 (2H, m).

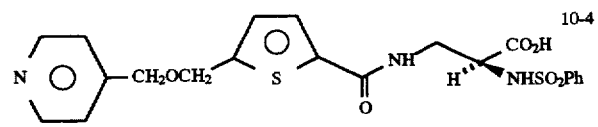

5-(4-Pyridylmethyloxymethyl)thiophene-2-carbonyl-2(S)-phenylsulfonylamino-β-alanine (10-4)

A solution of 10-3 (1 mmol) in 5 ml HCl was stirred for 16 hours at room temperature and the solvents were then removed to provide 10-4.

IN VITRO ACTIVITY

The test procedures employed to measure the anti-platelet aggregating activity of the compounds of the present invention are described below.

Blood was drawn into 0.1 volumes of acid citrate-dextrose (85 mM sodium citrate, 64 mM citric acid, 10 mM dextrose) by venipuncture from normal human volunteers. Platelet-rich plasma was prepared by centrifugation at 400×g for 12 minutes. PGE1(5mg/ml) was added and platelets were collected by centrifugation at 800×g for 12 minutes. The platelet pellet was resuspended into human platelet buffer (140 mM NaCl, 7.9 mM KCl, 3.3 mM $Na_2HPO_4$, 6 mM HEPES, 2% bovine serum albumin, 0.1% dextrose, pH 7.2) and filtered over Sepharose 2B that was previously equilibrated in human platelet buffer. Human fibrinogen (10-100 mg/ml) and CaCl$_2$ (1 mM) were added and aggregation was initiated by the addition of 10 mM ADP. Aggregation was monitored by the initial rate of increase of light transmittance.

The IC$_{50}$ (uM) of one compound claimed in the instant invention of the formula:

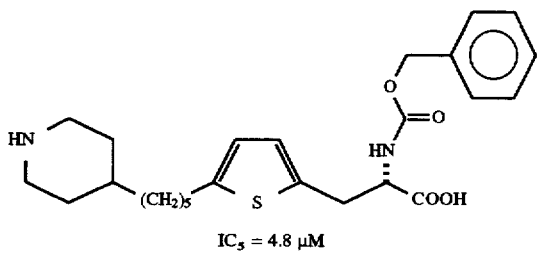

IC$_5$ = 4.8 μM demonstrates the fibrinogen inhibitory affect of the claimed compounds.

Therapeutic Treatment

Compounds of the invention may be used for inhibiting integrin protein-complex function relating to cell attachment activity. They may be administered to patients where inhibition of human or mammalian platelet aggregation or adhesion is desired.

Compounds of the invention may find utility in surgery on peripheral arteries (arterial grafts, carotid endaterectomy) and in cardiovascular surgery where manipulation of arteries and organs, and/or the interation of platelets with artificial surfaces, leads to platelet aggregation and consumption. The aggregated platelets may form thrombi and thromboemboli. Compounds of the invention may be administered to these surgical patients to prevent the formation of thrombi and thromboemboli.

Extracorporeal circulation is routinely used for cardiovascular surgery in order to oxygenate blood. Platelets adhere to surfaces of the extracorporael circuit. Adhesion is dependent on the interaction between gpII/IIIa on the platelet membranes and fibrinogen adsorbed to the surface of the circuit. (Lluszko et al., Amer. J. Physiol., 252:H, 615–621 (1987). Platelets released from artificial surfaces show impaired hemostatic function. Compounds of the invention may be administered to prevent adhesion.

Other applications of these compounds include prevention of platelet thrombosis, thromboembolism and reocclusion during and after thromboembolytic therapy and prevention of platelet thrombosis, thromboembolism and reocclusion after angioplasty of coronary and other arteries and after coronary artery bypass procedures. Compounds of the invention may also be used to prevent myocardial infarction and stroke.

These compounds may be administered by any convenient means which will result in its delivery into the blood stream in substantial amount including continuous intravenous or bolus injection or oral methods. Compositions of the invention include compounds of the invention and pharmaceutically acceptable carriers, e.g. saline, at a pH level of for example 7.4, suitable for achieving inhibition of platelet aggregation. They may also be used in combination with anticoagulants such as heparin or warfarin. Intravenous administration is presently comtemplated as the preferred administration route. They are soluble in water.

In one exemplary application, a suitable amount of compound is intravenously administered to a heart attack victim undergoing angioplasty. Administration occurs during or several minutes prior to angioplasty, and is in an amount sufficient to inhibit platelet aggregation, e.g. an amount which achieves a steady state plasma concentration of between about 0.01–30 uM, preferably between about 0.03–3 uM. When this amount is achieved, an infusion of between about 0.1–100 mg per kilo per min., preferably between about 1–20 mg per kilo per min. is maintained to inhibit platelet aggregation. Should the patient need to undergo bypass surgery, administration may be stopped immediately and will not cause complications during surgery that would be caused by other materials such as aspirin or monoclonal antibodies, the effects of which last hours after cessation of administration.

The present invention also includes a pharmaceutical compostion comprising compounds of the present invention and tissue type plasminogen activitor or streptokinase. The invention also includes a method for promoting thrombolysis and preventing reocclusion in a patient which comprises administering to the patient an effective amount of compositions of the invention.

The present invention may be embodied in other specific forms without departing from the spirit or essential attributes thereof. Thus, the specific examples described above should not be interpreted as limiting the scope of the present invention.

While the invention has been described and illustrated in reference to certain preferred embodiments thereof, those skilled in the art will appreciate that various changes, modifications and substitutions can be made therein without departing from the spirit and the scope of the invention. For example, effective dosages other than the preferred doses as set fourth hereinabove may be applicable as a consequence of variations in the responsiveness of the mammal being treated for severity of clotting disorders or emboli, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be intepreted as broadly as is reasonable.

What is claimed is:

1. A compound of the invention having the formula:

X—Y—Z-Aryl-A—B and the pharmaceutically acceptable salts thereof wherein:

Aryl is

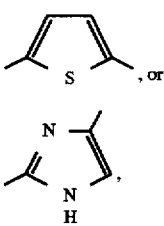

X is:

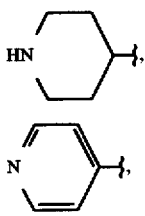

Y is:
 $C_{0-8}$ alkyl,
 $C_{4-10}$ cycloalkyl,
 $C_{0-8}$ alkyl-$NR^3$-CO-$C_{0-8}$ alkyl,
 $C_{0-8}$ alkyl-$CONR^3$-$C_{0-8}$ alkyl,
 $C_{0-8}$ alkyl-O-$C_{0-8}$ alkyl,
 $C_{0-8}$ alkyl-$S(O_p)$-$C_{0-8}$ alkyl,
 $C_{0-8}$ alkyl-$SO_2$-$NR^3$-$C_{0-8}$ alkyl,
 $C_{0-8}$ alkyl-$NR^3$-$SO_2$-$C_{0-8}$ alkyl,
 $C_{0-8}$ alkyl-CO-$C_{0-8}$ alkyl,
 $(CH_2)_{0-6}$ aryl$(CH_2)_{0-6}$,
 $(CH_2)_{0-6}$aryl-CO-$(CH_2)_{0-6}$,
 $C_{0-6}$ alkyl-aryl-$C_{0-6}$ alkyl,

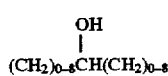

or $(CH_2)_{0-6}$aryl-CO-NH-$(CH_2)_{0-6}$;
wherein p is 0, 1, or 2;
Z and A are independently chosen from;
 $(CH_2)_m$, $(CH_2)_mO(CH_2)_n$, $(CH_2)_mNR^3(CH_2)_n$,

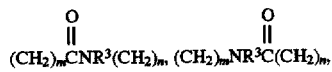

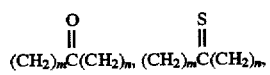

$(CH_2)_mSO_2(CH_2)_n$,
 $(CH_2)_mS(CH_2)_n$, $(CH_2)_mSO(CH_2)_n$, $(CH_2)_mSO_2NR^3(CH_2)_n$,
 $(CH_2)_mNR^3SO_2(CH_2)_n$, $(CH_2)_mCR^3{=}CR^4(CH_2)_n$,
 $(CH_2)_mC{\equiv}C(CH_2)_n$,
where m and n are integers independently chosen from 0–6;
B is

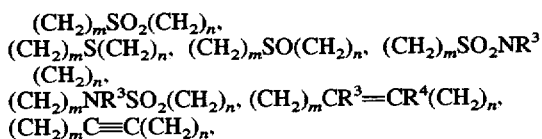

or

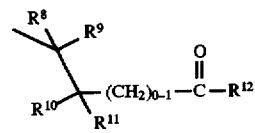

wherein:
$R^6$, $R^7$, $R^8$, $R^9$, $R^{10}$, and $R^{11}$ are independently chosen from
 hydrogen,
 fluorine,
 $C_{1-8}$ alkyl,
 hydroxyl,
 hydroxy $C_{1-6}$ alkyl,
 carboxy $C_{0-6}$ alkyl,
 $C_{1-6}$ alkyloxy,
 aryl $C_{1-6}$ alkyloxy,
 $C_{1-6}$ alkylcarbonyl $C_{0-6}$ alkyl,
 aryl $C_{0-6}$ alkylcarbonyl $C_{0-6}$ alkyl,
 $C_{1-6}$ alkylcarbonyloxy,
 aryl $C_{0-6}$ alkylcarbonyloxy,
 $C_{1-6}$ alkylaminocarbonyloxy,
 aryl $C_{0-6}$ alkylaminocarbonyloxy,
 $C_{3-8}$ cycloalkyl,
 aryl $C_{0-6}$ alkyl,
 $C_{0-6}$ alkylamino $C_{0-6}$ alkyl,
 $C_{0-6}$ dialkylamino $C_{0-6}$ alkyl,
 $C_{1-8}$ alkylsulfonylamino $C_{0-6}$ alkyl,
 aryl $C_{0-6}$ alkylsulfonylamino $C_{0-6}$ alkyl,
 aryl $C_{0-6}$ alkylamino,
 $C_{1-8}$ alkyloxycarbonylamino $C_{0-8}$ alkyl,
 aryl $C_{0-8}$ alkyloxycarbonylamino $C_{0-8}$ alkyl,
 $C_{1-8}$ alkylcarbonylamino $C_{0-6}$ alkyl,
 aryl $C_{0-6}$ alkylcarbonylamino $C_{0-6}$ alkyl,
 $C_{0-8}$ alkylaminocarbonylamino $C_{0-6}$ alkyl,
 aryl $C_{0-8}$ alkylaminocarbonylamino $C_{0-6}$ alkyl,
 $C_{0-8}$ alkylaminosulfonylamino $C_{0-6}$ alkyl,
 aryl $C_{0-8}$ alkylaminosulfonylamino $C_{0-6}$ alkyl,
 $C_{1-6}$ alkylsulfonyl $C_{0-6}$ alkyl,
 aryl $C_{0-6}$ alkylsulfonyl $C_{0-6}$ alkyl,
 $C_{1-6}$ alkylcarbonyl $C_{0-6}$ alkyl,
 aryl $C_{0-6}$ alkylcarbonyl $C_{0-6}$ alkyl,
 $C_{0-8}$ alkylaminosulfonyl $C_{0-8}$ alkyl,
 aryl $C_{0-8}$ alkylaminosulfonyl $C_{0-8}$ alkyl,
 $C_{0-8}$ alkylaminocarbonyl $C_{0-8}$ alkyl,
 aryl $C_{0-8}$ alkylaminocarbonyl $C_{0-8}$ alkyl,
 $C_{1-6}$ alkylthiocarbonylamino $C_{0-6}$ alkyl, or
 alkyl $C_{0-6}$ alkylthiocarbonylamino $C_{0-6}$ alkyl wherein the alkyl or aryl groups may be unsubstituted or substituted with one or more substituents selected from $R^1$ and $R^2$;
$R^1$, $R^2$, $R^3$, and $R^4$ are independently chosen from
 hydrogen,
 $C_{1-10}$ alkyl,
 aryl $C_{0-8}$ alkyl,
 oxy,
 thio,
 amino $C_{0-8}$ alkyl,
 $C_{1-3}$ acylamino $C_{0-8}$ alkyl,
 $C_{1-6}$ alkylamino $C_{0-8}$ alkyl,
 $C_{1-6}$ dialkylamino $C_{0-8}$ alkyl,
 $C_{1-4}$ alkoxy $C_{0-6}$ alkyl,
 carboxy $C_{0-6}$ alkyl,
 $C_{1-4}$ alkoxycarbonyl $C_{0-6}$ alkyl,
 carboxy $C_{0-6}$ alkyloxy or
 hydroxy $C_{0-6}$ alkyl;
$R^{12}$ is chosen from
 hydroxy,
 $C_{1-8}$ alkyloxy,
 aryl $C_{0-6}$ alkyloxy,
 $C_{1-8}$ alkylcarbonyloxy $C_{1-4}$ alkyloxy,
 aryl $C_{1-8}$ alkylcarbonyloxy $C_{1-4}$ alkyloxy, or
 an L- or D-amino acid joined by an amide linkage and wherein the carboxylic acid moiety of said amino acid is as the free acid or is esterified by $C_{1-6}$ alkyl provided that when Aryl is

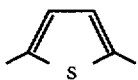

Y is not $C_{0-8}$ alkyl-$CONR^3$-$C_{0-8}$ alkyl, Z is not

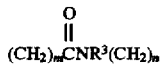

and A is not $(CH_2)_m$.

2. A compound of claim 1 wherein —Y—Z— is:
—$(CH_2)_5$—,
—$CH_2OCH_2$—,
—$CH_2$—,
—$(CH_2)_2OCH_2$—,
—$CH_2CH_2N(CH_3)CH_2$—,
$(CH_2)_3SO_2$—,
—$(CH_2)_3N(CH_3)CH_2$—,
—$(CH_2)_3S$—,
—$CH_2CH_2NHCH_2$—,
—$CH_2CH_2S$—,
—$CH_2CH_2O$—,
—$(CH_2)_4O$— or
—$(CH_2)_3O$—.

3. A compound selected from the group consisting of:
3-{5-[5-(4-Piperidinyl)pentyl]thien-2-yl}-2-(N-benzyloxycarbonylamino)propanoic acid,
N-2-(4-Piperidinyl)ethyl-N'-3-[2(S)-n-butylsulfonylaminopropanoic acid]-2,5-thiophenedicarboxamide,
N-2-(4-Piperidinyl)ethyl-N'-(2-carboxyethyl)-2,5-thiophenedicarboxamide,
2-[2-(Piperidin-4-yl)ethylthio]imidazole-4-carbonyl-2(S)-phenylsulfonylamino-β-alanine,
2-[3-(Piperidin-4-yl)propylthio]thiophene-5-carbonyl-2(S)-phenylsulfonylamino-β-alanine,
5-[(2-N,N-Diethylaminoethyl)oxymethyl]thiophene-2-carbonyl-2(S)-phenylsulfonylamino-β-alanine methyl ester,
5-[(2-N,N-Diethylaminoethyl)oxymethyl]thiophene-2-carbonyl-2(S)-phenylsulfonylamino-β-alanine,
5-(4-Pyridylmethyloxymethyl)thiophene-2-carbonyl-2(S)-phenylsulfonylamino-β-alanine methyl ester, and
5-(4-Pyridylmethyloxymethyl)thiophene-2-carbonyl-2(S)-phenylsulfonylamino-β-alanine,
2-[3-(Piperidin-4-yl)propyl-1-sulfonyl]thiophene-5-carbonyl-2(S)-phenylsulfonylamino-β-alanine,
and the pharmaceutically acceptable salts thereof.

4. A method of blocking fibrinogen from acting at its receptor site in a human, comprising administering a pharmacologically effective amount of a compound as claimed in claim 1.

5. A method of preventing thrombus and embolus formation in a human, in need thereof, comprising administering a pharmacologically effective amount of a compound as claimed in claim 1.

6. A method of treating thrombus and embolus formation in a human, in need thereof, comprising administering a pharmacologically effective amount of a compound as claimed in claim 1.

7. A method of inhibiting aggregation of blood platelets in a mammal, including a human, comprising administering a pharmacologically effective amount of a compound as claimed in claim 1.

8. A pharmaceutical composition, comprising a compound as claimed in claim 1, and a pharmaceutically acceptable carrier.

9. A method of blocking fibrinogen from acting at its receptor site in a human, comprising administering a pharmacologically effective amount of a compound as claimed in claim 3.

10. A method of preventing thrombus and embolus formation in a mammal, including a human, in need thereof, comprising administering a pharmacologically effective amount of a compound as claimed in claim 3.

11. A method of treating thrombus and embolus formation in a mammal, including a human, in need thereof, comprising administering a pharmacologically effective amount of a compound as claimed in claim 3.

12. A method of inhibiting aggregation of blood platelets in a mammal, including a human, comprising administering a pharmacologically effective amount of a compound as claimed in claim 3.

13. A pharmaceutical composition, comprising a compound as claimed in claim 3, and a pharmaceutically acceptable carrier.

* * * * *